United States Patent
Sanny et al.

(10) Patent No.: US 9,309,540 B2
(45) Date of Patent: Apr. 12, 2016

(54) INCREASED ETHANOL PRODUCTION BY GENETIC ENGINEERING OF MICROORGANISMS TO EXPRESS HEMOGLOBIN

(71) Applicant: Illinois Institute of Technology

(72) Inventors: Tony Sanny, Boulder, CO (US); Benjamin C. Stark, Oak Park, IL (US)

(73) Assignee: ILLINOIS INSTITUTE OF TECHNOLOGY, Chicago, IL (US)

( * ) Notice: Subject to any disclaimer, the term of this patent is extended or adjusted under 35 U.S.C. 154(b) by 0 days.

(21) Appl. No.: 14/720,436

(22) Filed: May 22, 2015

(65) Prior Publication Data

US 2015/0252388 A1 Sep. 10, 2015

Related U.S. Application Data

(63) Continuation-in-part of application No. 14/340,129, filed on Jul. 24, 2014, now Pat. No. 9,045,779.

(51) Int. Cl.
| | |
|---|---|
| *C12P 7/06* | (2006.01) |
| *C12N 1/22* | (2006.01) |
| *C07K 14/22* | (2006.01) |
| *C12N 9/04* | (2006.01) |
| *C12N 9/02* | (2006.01) |
| *C12N 9/92* | (2006.01) |

(52) U.S. Cl.
CPC .............. *C12P 7/065* (2013.01); *C07K 14/22* (2013.01); *C12N 1/22* (2013.01); *C12N 9/0006* (2013.01); *C12N 9/0008* (2013.01); *C12N 9/92* (2013.01); *C12P 7/06* (2013.01); *Y02E 50/17* (2013.01)

(58) Field of Classification Search
CPC ........ C07K 14/22; C12N 1/22; C12N 9/0006; C12N 9/0008; C12N 9/92; C12P 7/065; Y02E 50/17
See application file for complete search history.

(56) References Cited

PUBLICATIONS

Ruohonen et al., Enzyme and Microbial Technology 39:6-14, 2006.*
Kuyper et al., FEMS Yeast Research 4:655-664, 2004.*
Tsai et al., Biotechnology and Bioengineering 49:139-150, 1996.*
Bratbark et al., Applied and Environmental Microbiology 48(4):755-757, 1984.*

* cited by examiner

*Primary Examiner* — Delia Ramirez
(74) *Attorney, Agent, or Firm* — Swanson & Bratschun, L.L.C.

(57) ABSTRACT

The present disclosure describes novel bacterial strains which express a pyruvate decarboxylase gene and at least one alcohol dehydrogenase gene from a bacteria of the genus *Zymomonas* and also express a hemoglobin gene from a bacteria of the genus *Vitreoscilla*. The present disclosure further describes methods for producing fermentation products with a microorganism which expresses a pyruvate decarboxylase gene and at least one alcohol dehydrogenase gene from a bacteria of the genus *Zymomonas* and also express a hemoglobin gene from a bacteria of the genus *Vitreoscilla*. Further the present disclosure describes methods for increasing production of a fermentation product comprising genetically engineering a microorganism which expresses a xylose isomerase gene to also express a hemoglobin gene from a bacteria of the genus *Vitreoscilla*.

8 Claims, 7 Drawing Sheets

1) λ DNA – HindIII digest
2) PCR *pdc+adhb* and *vgb+Tc$^R$* on FBR5/pTS3 DNA prep (clone 2a)
3) PCR *pdc+adhb* and *vgb+Tc$^R$* on FBR5/pTS3 DNA prep (clone 2b)
4) PCR of *vgb+Tc$^R$* on pTS3 (positive control) and PCR of *pdc+adhb* on pLOI297 (positive control)
5) PCR of *vgb+Tc$^R$* on dH$_2$0 (negative control) and PCR of *pdc+adhb* on dH2O (negative control)

Figure 5.

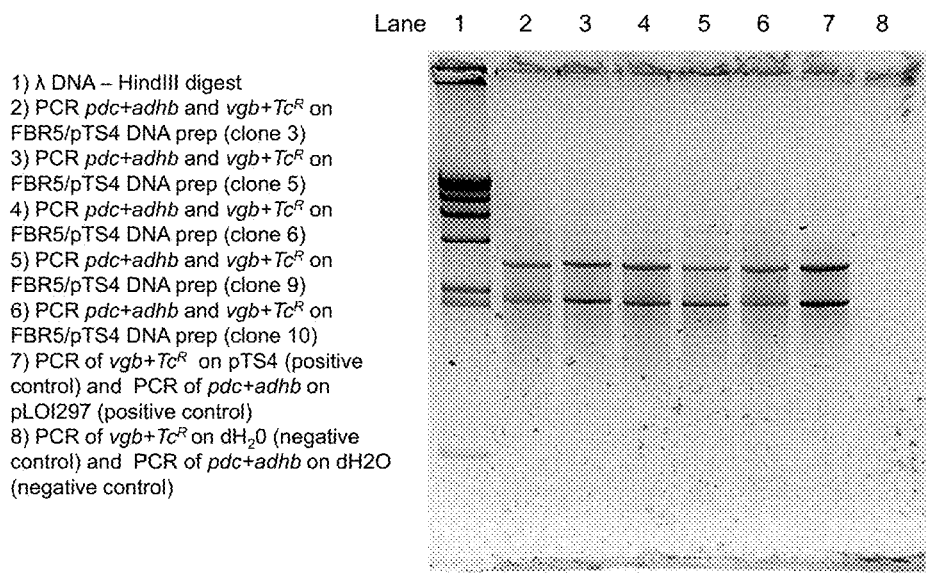

1) λ DNA – HindIII digest
2) PCR *pdc+adhb* and *vgb+Tc$^R$* on FBR5/pTS4 DNA prep (clone 3)
3) PCR *pdc+adhb* and *vgb+Tc$^R$* on FBR5/pTS4 DNA prep (clone 5)
4) PCR *pdc+adhb* and *vgb+Tc$^R$* on FBR5/pTS4 DNA prep (clone 6)
5) PCR *pdc+adhb* and *vgb+Tc$^R$* on FBR5/pTS4 DNA prep (clone 9)
6) PCR *pdc+adhb* and *vgb+Tc$^R$* on FBR5/pTS4 DNA prep (clone 10)
7) PCR of *vgb+Tc$^R$* on pTS4 (positive control) and PCR of *pdc+adhb* on pLOI297 (positive control)
8) PCR of *vgb+Tc$^R$* on dH$_2$0 (negative control) and PCR of *pdc+adhb* on dH2O (negative control)

Figure 6.

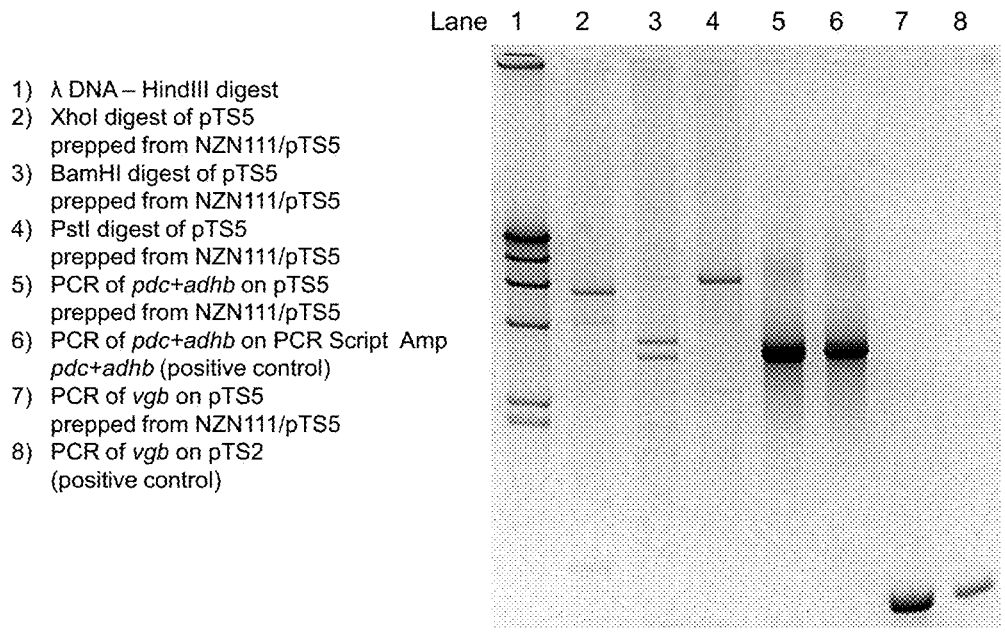

1) λ DNA – HindIII digest
2) XhoI digest of pTS5 prepped from NZN111/pTS5
3) BamHI digest of pTS5 prepped from NZN111/pTS5
4) PstI digest of pTS5 prepped from NZN111/pTS5
5) PCR of *pdc+adhb* on pTS5 prepped from NZN111/pTS5
6) PCR of *pdc+adhb* on PCR Script Amp *pdc+adhb* (positive control)
7) PCR of *vgb* on pTS5 prepped from NZN111/pTS5
8) PCR of *vgb* on pTS2 (positive control)

SEQUENCE LISTING

<160> NUMBER OF SEQ ID NOS: 22

<210> SEQ ID NO 1
<211> LENGTH: 745
<212> TYPE: DNA
<213> ORGANISM: Vitreoscilla stercoraria
<220> FEATURE:
<221> NAME/KEY: misc_feature
<223> OTHER INFORMATION: gene encoding hemoglobin

<400> SEQUENCE: 1

```
aagcttacag gacgctgggg ttaaaagtat ttgagttttg atgtggatta agttttaaga      60
ggcaataaag attataataa gtgctgctac accatactga tgtatggcaa aaccataata     120
atgaacttaa ggaagaccct catgttagac cagcaaacca ttaacatcat caaagccact     180
gttcctgtat tgaaggagca tggcgttacc attaccacga cttttttataa aaacttgttt     240
gccaaacacc ctgaagtacg tcctttgttt gatatgggtc gccaagaatc tttggagcag     300
cctaaggctt tggcgatgac ggtattggcg gcagcgcaaa acattgaaaa tttgccagct     360
attttgcctg cggtcaaaaa aattgcagtc aaacattgtc aagcaggcgt ggcagcagcg     420
cattatccga ttgtcggtca agaattgttg ggtgcgatta agaagtatt gggcgatgcc     480
gcaaccgatg acattttgga cgcgtggggc aaggcttatg gcgtgattgc agatgtgttt     540
attcaagtgg aagcagattt gtacgctcaa gcggttgaat aaagtttcag gccgctttca     600
ggacataaaa aacgcaccat aaggtggtct ttttacgtct gatatttaca cagcagcagt     660
ttggctgttg gccaaaactt gggacaaata ttgccctgtg taagagcccg ccgttgctgc     720
gacgtcttca ggtgtgcctt ggcat                                           745
```

<210> SEQ ID NO 2
<211> LENGTH: 146
<212> TYPE: PRT
<213> ORGANISM: Vitreoscilla stercoraria
<220> FEATURE:
<221> NAME/KEY: misc_feature
<223> OTHER INFORMATION: hemoglobin

<400> SEQUENCE: 2

```
Met Leu Asp Gln Gln Thr Ile Asn Ile Ile Lys Ala Thr Val Pro Val
1               5                   10                  15

Leu Lys Glu His Gly Val Thr Ile Thr Thr Thr Phe Tyr Lys Asn Leu
            20                  25                  30

Phe Ala Lys His Pro Glu Val Arg Pro Leu Phe Asp Met Gly Arg Gln
        35                  40                  45

Glu Ser Leu Glu Gln Pro Lys Ala Leu Ala Met Thr Val Leu Ala Ala
    50                  55                  60

Ala Gln Asn Ile Glu Asn Leu Pro Ala Ile Leu Pro Ala Val Lys Lys
65                  70                  75                  80

Ile Ala Val Lys His Cys Gln Ala Gly Val Ala Ala His Tyr Pro
            85                  90                  95

Ile Val Gly Gln Glu Leu Leu Gly Ala Ile Lys Glu Val Leu Gly Asp
            100                 105                 110

Ala Ala Thr Asp Asp Ile Leu Asp Ala Trp Gly Lys Ala Tyr Gly Val
        115                 120                 125

Ile Ala Asp Val Phe Ile Gln Val Glu Ala Asp Leu Tyr Ala Gln Ala
    130                 135                 140

Val Glu
145
```

<210> SEQ ID NO 3
<211> LENGTH: 1707
<212> TYPE: DNA
<213> ORGANISM: Zymomonas mobilis
<220> FEATURE:
<221> NAME/KEY: misc_feature
<223> OTHER INFORMATION: pyruvate decarboxylase gene

<400> SEQUENCE: 3

| | | | | | |
|---|---|---|---|---|---|
| atgagttata | ctgtcggtac | ctatttagcg | gagcggcttg | tccagattgg | tctcaagcat | 60 |
| cacttcgcag | tcgcgggcga | ctacaacctc | gtccttcttg | acaacctgct | tttgaacaaa | 120 |
| aacatggagc | aggtttattg | ctgtaacgaa | ctgaactgcg | gtttcagtgc | agaaggttat | 180 |
| gctcgtgcca | aaggcgcagc | agcagccgtc | gttacctaca | cgtcggtgc | gctttccgca | 240 |
| tttgatgcta | tcggtggcgc | ctatgcagaa | aaccttccgg | ttatcctgat | ctccggtgct | 300 |
| ccgaacaaca | atgatcacgc | tgctggtcac | gtgttgcatc | acgctcttgg | caaaaccgac | 360 |
| tatcactatc | agttggaaat | ggccaagaac | atcacggccg | cagctgaagc | gatttacacc | 420 |
| ccagaagaag | ctccggctaa | aatcgatcac | gtgattaaaa | ctgctcttcg | tgagaagaag | 480 |
| ccggtttatc | tcgaaatcgc | ttgcaacatt | gcttccatgc | cctgcgccgc | tcctggaccg | 540 |
| gcaagcgcat | tgttcaatga | cgaagccagc | gacgaagctt | ctttgaatgc | agcggttgaa | 600 |
| gaaacgctga | aattcatcgc | caaccgcgac | aaagttgccg | tcctcgtcgg | cagcaagctg | 660 |
| cgcgcagctg | gtgctgaaga | agctgctgtc | aaatttgctg | atgctctcgg | tggcgcagtt | 720 |
| gctaccatgg | ctgctgcaaa | aagcttcttc | ccagaagaaa | acccgcatta | catcggtacc | 780 |
| tcatggggtg | aagtcagcta | tccgggcgtt | gaaaagacga | tgaaagaagc | cgatgcggtt | 840 |
| atcgctctgg | ctcctgtctt | caacgactac | tccaccactg | gttggacgga | tattcctgat | 900 |
| cctaagaaac | tggttctcgc | tgaaccgcgt | tctgtcgtcg | ttaacggcgt | tcgcttcccc | 960 |
| agcgttcatc | tgaaagacta | tctgacccgt | ttggctcaga | agtttccaa | gaaaccggt | 1020 |
| gctttggact | tcttcaaatc | cctcaatgca | ggtgaactga | agaaagccgc | tccggctgat | 1080 |
| ccgagtgctc | cgttggtcaa | cgcagaaatc | gcccgtcagg | tcgaagctct | tctgaccccg | 1140 |
| aacacgacgg | ttattgctga | aaccggtgac | tcttggttca | atgctcagcg | catgaagctc | 1200 |
| ccgaacggtg | ctcgcgttga | atatgaaatg | cagtggggtc | acatcggttg | gtccgttcct | 1260 |
| gccgccttcg | gttatgccgt | cggtgctccg | gaacgtcgca | acatcctcat | ggttggtgat | 1320 |
| ggttccttcc | agctgacggc | tcaggaagtc | gctcagatgg | ttcgcctgaa | actgccggtt | 1380 |
| atcatcttct | tgatcaataa | ctatggttac | accatcgaag | ttatgatcca | tgatggtccg | 1440 |
| tacaacaaca | tcaagaactg | ggattatgcc | ggtctgatgg | aagtgttcaa | cggtaacggt | 1500 |
| ggttatgaca | gcggtgctgg | taaaggcctg | aaggctaaaa | ccggtggcga | actggcagaa | 1560 |
| gctatcaagg | ttgctctggc | aaacaccgac | ggcccaaccc | tgatcgaatg | cttcatcggt | 1620 |
| cgtgaagact | gcactgaaga | attggtcaaa | tggggtaagc | gcgttgctgc | cgccaacagc | 1680 |
| cgtaagcctg | ttaacaagct | cctctag | | | | 1707 |

<210> SEQ ID NO 4
<211> LENGTH: 568
<212> TYPE: PRT
<213> ORGANISM: Zymomonas mobilis
<220> FEATURE:
<221> NAME/KEY: misc_feature
<223> OTHER INFORMATION: pyruvate decarboxylase

<400> SEQUENCE: 4

```
Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
                100                 105                 110

His His Ala Leu Gly Lys Thr Asp Tyr His Tyr Gln Leu Glu Met Ala
            115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
    195                 200                 205

Arg Asp Lys Val Ala Val Leu Val Gly Ser Lys Leu Arg Ala Ala Gly
210                 215                 220

Ala Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Asn Gly Val Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
    370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415
```

```
Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565
```

```
<210> SEQ ID NO 5
<211> LENGTH: 1152
<212> TYPE: DNA
<213> ORGANISM: Zymomonas mobilis
<220> FEATURE:
<221> NAME/KEY: misc_feature
<223> OTHER INFORMATION: alcohol dehydrogenase II (AdhB) gene

<400> SEQUENCE: 5
atggcttctt caactttta tattcctttc gtcaacgaaa tgggcgaagg ttcgcttgaa      60
aaagcaatca aggatcttaa cggcagcggc tttaaaaatg cgctgatcgt ttctgatgct     120
ttcatgaaca atccggtgt tgtgaagcag gttgctgacc tgttgaaagc acagggtatt     180
aattctgctg tttatgatgg cgttatgccg aacccgactg ttaccgcagt tctggaaggc     240
cttaagatcc tgaaggataa caattcagac ttcgtcatct ccctcggtgg tggttctccc     300
catgactgcg ccaaagccat cgctctggtc gcaaccaatg gtggtgaagt caaagactac     360
gaaggtatcg acaaatctaa gaaacctgcc ctgcctttga tgtcaatcaa cacgacggct     420
ggtacggctt ctgaaatgac gcgtttctgc atcatcactg atgaagtccg tcacgttaag     480
atggccattg ttgaccgtca cgttaccccg atggtttccg tcaacgatcc tctgttgatg     540
gttggtatgc caaaaggcct gaccgccgcc accggtatgg atgctctgac ccacgcattt     600
gaagcttatt cttcaacggc agctactccg atcaccgatg cttgcgcctt gaaggctgcg     660
tccatgatcg ctaagaatct gaagaccgct tgcgacaacg taaggatat gccagctcgt      720
gaagctatgg cttatgccca attcctcgct ggtatggcct tcaacaacgc ttcgcttggt     780
tatgtccatg ctatggctca ccagttgggc ggctactaca acctgccgca tggtgtctgc     840
aacgctgttc tgcttccgca tgttctggct tataacgcct ctgtcgttgc tggtcgtctg     900
aaagacgttg gtgttgctat gggtctcgat atcgccaatc tcggtgataa agaaggcgca     960
gaagccacca ttcaggctgt cgcgatctg gctgcttcca ttggtattcc agcaaatctg      1020
accgagctgg gtgctaagaa agaagatgtg ccgcttcttg ctgaccacgc tctgaaagat     1080
gcttgtgctc tgaccaaccc gcgtcagggt gatcagaaag aagttgaaga actcttcctg     1140
```
agcgctttct aa 1152

<210> SEQ ID NO 6
<211> LENGTH: 383
<212> TYPE: PRT
<213> ORGANISM: Zymomonas mobilis
<220> FEATURE:
<221> NAME/KEY: misc_feature
<223> OTHER INFORMATION: alcohol dehydrogenase II (AdhB)

<400> SEQUENCE: 6

```
Met Ala Ser Ser Thr Phe Tyr Ile Pro Phe Val Asn Glu Met Gly Glu
 1               5                  10                  15

Gly Ser Leu Glu Lys Ala Ile Lys Asp Leu Asn Gly Ser Gly Phe Lys
            20                  25                  30

Asn Ala Leu Ile Val Ser Asp Ala Phe Met Asn Lys Ser Gly Val Val
        35                  40                  45

Lys Gln Val Ala Asp Leu Leu Lys Ala Gln Gly Ile Asn Ser Ala Val
    50                  55                  60

Tyr Asp Gly Val Met Pro Asn Pro Thr Val Thr Ala Val Leu Glu Gly
65                  70                  75                  80

Leu Lys Ile Leu Lys Asp Asn Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
        115                 120                 125

Pro Ala Leu Pro Leu Met Ser Ile Asn Thr Thr Ala Gly Thr Ala Ser
    130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
            180                 185                 190

Met Asp Ala Leu Thr His Ala Phe Glu Ala Tyr Ser Ser Thr Ala Ala
        195                 200                 205

Thr Pro Ile Thr Asp Ala Cys Ala Leu Lys Ala Ala Ser Met Ile Ala
    210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Tyr
            260                 265                 270

Tyr Asn Leu Pro His Gly Val Cys Asn Ala Val Leu Leu Pro His Val
        275                 280                 285

Leu Ala Tyr Asn Ala Ser Val Val Ala Gly Arg Leu Lys Asp Val Gly
    290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
            340                 345                 350
```

Leu Ala Asp His Ala Leu Lys Asp Ala Cys Ala Leu Thr Asn Pro Arg
        355                 360                 365

Gln Gly Asp Gln Lys Glu Val Glu Glu Leu Phe Leu Ser Ala Phe
    370                 375                 380

<210> SEQ ID NO 7
<211> LENGTH: 1014
<212> TYPE: DNA
<213> ORGANISM: Zymomonas mobilis
<220> FEATURE:
<221> NAME/KEY: misc_feature
<223> OTHER INFORMATION: alcohol dehydrogenase I (adhA) gene

<400> SEQUENCE: 7

| | | | | | |
|---|---|---|---|---|---|
| atgaaagcag | ccgtcataac | taaagatcat | acgatcgaag | tgaaagacac | caaattacgc | 60 |
| cctctgaaat | acggggaagc | gcttttggaa | atggaatatt | gcggggtatg | tcataccgat | 120 |
| ctccatgtga | aaacggggga | tttcggcgat | gaaaccggca | gaattaccgg | ccatgaaggt | 180 |
| atcggtatcg | tcaagcaggt | cggggaaggg | gttacttctc | tgaaagccgg | tgaccgcgcc | 240 |
| agtgttgcat | ggttcttcaa | aggctgcggc | cattgcgaat | attgtgtcag | cgggaatgaa | 300 |
| acgctttgcc | gcaacgttga | aaatgccggt | tatacgttg | acggcgctat | ggcagaagaa | 360 |
| tgcatcgtcg | ttgccgatta | ctcggtcaag | gtgccagatg | tcttgatcc | tgcggttgcc | 420 |
| agcagcatca | cttgcgcggg | tgtaaccacc | tataaagcag | tcaaagtttc | tcagatacag | 480 |
| ccgggacaat | ggctggccat | ctatggcttg | ggcggtttag | gcaatctagc | ccttcaatat | 540 |
| gccaagaatg | ttttcaacgc | caaagtgatc | gcgatcgatg | tcaatgatga | acagctcgct | 600 |
| tttgccaaag | agttgggcgc | agatatggtc | atcaatccga | aaaacgaaga | tgctgccaaa | 660 |
| atcattcagg | aaaaagtcgg | cggcgcacat | gcgacggtgg | tgacggctgt | tgccaaatcc | 720 |
| gcctttaact | cggctgttga | ggctatccgc | gcgggtggcc | gtgttgtcgc | cgttggtctg | 780 |
| cctcctgaaa | aatggatttt | gagcattcct | cgtttggtgc | ttgacggtat | cgaagtccta | 840 |
| ggttccttgg | tcggaacgcg | ggaagatttg | aaagaggcct | tccagtttgc | agccgaaggt | 900 |
| aaggtcaagc | cgaaagttac | caagcgtaaa | gtcgaagaaa | tcaaccaaat | ctttgacgaa | 960 |
| atggaacatg | gtaaattcac | aggccgtatg | gttgttgatt | ttacccatca | ctag | 1014 |

<210> SEQ ID NO 8
<211> LENGTH: 337
<212> TYPE: PRT
<213> ORGANISM: Zymomonas mobilis
<220> FEATURE:
<221> NAME/KEY: misc_feature
<223> OTHER INFORMATION: alcohol dehydrogenase I (adhA)

<400> SEQUENCE: 8

Met Lys Ala Ala Val Ile Thr Lys Asp His Thr Ile Glu Val Lys Asp
1               5                   10                  15

Thr Lys Leu Arg Pro Leu Lys Tyr Gly Glu Ala Leu Leu Glu Met Glu
            20                  25                  30

Tyr Cys Gly Val Cys His Thr Asp Leu His Val Lys Asn Gly Asp Phe
        35                  40                  45

Gly Asp Glu Thr Gly Arg Ile Thr Gly His Glu Gly Ile Gly Ile Val
    50                  55                  60

Lys Gln Val Gly Glu Gly Val Thr Ser Leu Lys Ala Gly Asp Arg Ala
65                  70                  75                  80

Ser Val Ala Trp Phe Phe Lys Gly Cys Gly His Cys Glu Tyr Cys Val

```
              85                  90                  95
Ser Gly Asn Glu Thr Leu Cys Arg Asn Val Glu Asn Ala Gly Tyr Thr
            100                 105                 110

Val Asp Gly Ala Met Ala Glu Glu Cys Ile Val Val Ala Asp Tyr Ser
        115                 120                 125

Val Lys Val Pro Asp Gly Leu Asp Pro Ala Val Ala Ser Ser Ile Thr
    130                 135                 140

Cys Ala Gly Val Thr Thr Tyr Lys Ala Val Lys Val Ser Gln Ile Gln
145                 150                 155                 160

Pro Gly Gln Trp Leu Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Ala Phe Ala Lys Glu Leu Gly Ala Asp
        195                 200                 205

Met Val Ile Asn Pro Lys Asn Glu Asp Ala Ala Lys Ile Ile Gln Glu
    210                 215                 220

Lys Val Gly Gly Ala His Ala Thr Val Val Thr Ala Val Ala Lys Ser
225                 230                 235                 240

Ala Phe Asn Ser Ala Val Glu Ala Ile Arg Ala Gly Gly Arg Val Val
                245                 250                 255

Ala Val Gly Leu Pro Pro Glu Lys Met Asp Leu Ser Ile Pro Arg Leu
            260                 265                 270

Val Leu Asp Gly Ile Glu Val Leu Gly Ser Leu Val Gly Thr Arg Glu
        275                 280                 285

Asp Leu Lys Glu Ala Phe Gln Phe Ala Ala Glu Gly Lys Val Lys Pro
    290                 295                 300

Lys Val Thr Lys Arg Lys Val Glu Glu Ile Asn Gln Ile Phe Asp Glu
305                 310                 315                 320

Met Glu His Gly Lys Phe Thr Gly Arg Met Val Val Asp Phe Thr His
                325                 330                 335

His
```

<210> SEQ ID NO 9
<211> LENGTH: 1323
<212> TYPE: DNA
<213> ORGANISM: Escherichia coli
<220> FEATURE:
<221> NAME/KEY: misc_feature
<223> OTHER INFORMATION: Xylose isomerase gene

<400> SEQUENCE: 9

```
ttatttgtcg aacagataat gatttaccag attttccagt tgctcctggc gaccactctg      60
atgcaccgga gacaaattat gttcctgagc atatttggct aaatctgcca gtgacatttg     120
gcctttcagg atttgctggc ctaattcact attccagccg gaataacgct gcgcgatgcg     180
tttatccagc tcgccatctt caatcatgcg cgctgcaatt ttcagcgcca acgccatcgt     240
atccatcgcg ccgatatgac cgtaaaacag atcatattta tcagtacttt gacgacgtac     300
tttggcatcg aagttcagac caccggtggt gaaaccgcct gctttgagaa tttcatacat     360
caccagcgca ttctcttcca cactgttcgg gaactggtcg gtgtcccagc ccagttgcgc     420
atcgccacgg ttggcgtcga cagaaccgaa caggccaagc gcaatggcgg tggctatttc     480
atgatggaaa gagtgacctg ccagcgtcgc gtggttagct caatattca gtttaatctc     540
ttttttccaga ccaaactgtt tcaggaagcc atagaccgtc gcagcatcgt aatcatattg     600
```

```
atgtttggtc ggttcttgcg gtttcggttc gataagcaac gtgccctgga aaccgatttt    660
atgtttatgc tcaaccacca tctgcataaa gcggcccagc tgttcacgct cctggcgcaa    720
gtcggtattt aacagcgttt cgtaaccttc acgaccaccc cacaggacat agttttcacc    780
gcccaattta tggttgctt ccatcgctgt aacaacttgc gttgccgccc aactgaagac    840
ttcaggatct gggttcgtcg ccgcacccgc gccatagcga gggtttgtaa agcagttagc    900
agttccccac agcagcttca cgccgctctc ttcttgcttg cctgccagga catcaaccat    960
ttgcgcaaaa ttattgatgt actcttttaa cgacgcgccc tcaggggaaa catccacatc    1020
gtggaagcaa taaatggca catgtaactt gtggaaaaac tcaaatgcga catctgcttt    1080
acgcttcgcc aacgccagtg cctcaccagg ctgctgccac ggacgattaa acgcccccac    1140
accaaacata tccgccccgt tccagcagaa ggtgtgccag tagcaggcgg caaaacgcaa    1200
gtgctcttcc atacgcttgc ccaacaccag ttcgtcggga ttgtagtgac ggaatgctaa    1260
cgggtttgag gattttgagc cttcataacg aacgcgatcg agctggtcaa aataggcttg    1320
cat                                                                 1323
```

<210> SEQ ID NO 10
<211> LENGTH: 440
<212> TYPE: PRT
<213> ORGANISM: Escherichia coli
<220> FEATURE:
<221> NAME/KEY: misc_feature
<223> OTHER INFORMATION: Xylose isomerase

<400> SEQUENCE: 10

```
Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220
```

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
            245                 250                 255

Phe Gly Leu Glu Lys Glu Ile Lys Leu Asn Ile Glu Ala Asn His Ala
        260                 265                 270

Thr Leu Ala Gly His Ser Phe His His Glu Ile Ala Thr Ala Ile Ala
    275                 280                 285

Leu Gly Leu Phe Gly Ser Val Asp Ala Asn Arg Gly Asp Ala Gln Leu
290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
            325                 330                 335

Asn Phe Asp Ala Lys Val Arg Arg Gln Ser Thr Asp Lys Tyr Asp Leu
        340                 345                 350

Phe Tyr Gly His Ile Gly Ala Met Asp Thr Met Ala Leu Ala Leu Lys
    355                 360                 365

Ile Ala Ala Arg Met Ile Glu Asp Gly Glu Leu Asp Lys Arg Ile Ala
370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His Asn
            405                 410                 415

Leu Ser Pro Val His Gln Ser Gly Arg Gln Glu Gln Leu Glu Asn Leu
        420                 425                 430

Val Asn His Tyr Leu Phe Asp Lys
    435                 440

<210> SEQ ID NO 11
<211> LENGTH: 37
<212> TYPE: DNA
<213> ORGANISM: Artificial Sequence
<220> FEATURE:
<223> OTHER INFORMATION: Primer

<400> SEQUENCE: 11
aaactgcagg ttaaaagtat ttgagttttg atgtgga                           37

<210> SEQ ID NO 12
<211> LENGTH: 47
<212> TYPE: DNA
<213> ORGANISM: Artificial Sequence
<220> FEATURE:
<223> OTHER INFORMATION: Primer

<400> SEQUENCE: 12
ccaatgcatt ggttctgcag gtgtaaatat cagacgtaaa aagacca                47

<210> SEQ ID NO 13
<211> LENGTH: 48
<212> TYPE: DNA
<213> ORGANISM: Artificial Sequence
<220> FEATURE:
<223> OTHER INFORMATION: Primer

<400> SEQUENCE: 13
aaaactgcag aaaacccggg ctcttccttt ttcaatatta ttgaagca               48

<210> SEQ ID NO 14
<211> LENGTH: 59
<212> TYPE: DNA
<213> ORGANISM: Artificial Sequence
<220> FEATURE:
<223> OTHER INFORMATION: Primer

<400> SEQUENCE: 14
tgcattggct gcagtttccc gggttttttga attcatatgt tctgccaagg gttggtttg    59

<210> SEQ ID NO 15
<211> LENGTH: 53
<212> TYPE: DNA
<213> ORGANISM: Artificial Sequence
<220> FEATURE:
<223> OTHER INFORMATION: Primer

<400> SEQUENCE: 15
cccaagcttt tgacagctta tcatcgataa gctataatgc ggtagtttat cac    53

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
cccaagctta tatgttctgc caagggttgg tttg    34

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
ggcgaattcc tgcaaggcga ttaagttgg    29

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
ggcgaattcc aaggcacacc tgaagacg    28

<210> SEQ ID NO 19
<211> LENGTH: 32
<212> TYPE: DNA
<213> ORGANISM: Artificial Sequence
<220> FEATURE:
<223> OTHER INFORMATION: Primer

<400> SEQUENCE: 19
aaaggatccg cgcaacgtaa ttaatgtgag tt    32

<210> SEQ ID NO 20
<211> LENGTH: 26
<212> TYPE: DNA
<213> ORGANISM: Artificial Sequence
<220> FEATURE:
<223> OTHER INFORMATION: Primer

```
<400> SEQUENCE: 20
tttggatccc caaatggcaa attatt                                            26

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
ggcctcgagc tgcaaggcga ttaagttgg                                         29

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
ggcctcgagc aaggcacacc tgaagacg                                          28
```

INCREASED ETHANOL PRODUCTION BY GENETIC ENGINEERING OF MICROORGANISMS TO EXPRESS HEMOGLOBIN

RELATED APPLICATIONS

This application is a continuation-in-part application of U.S. application Ser. No. 14/340,129, filed on Jul. 24, 2014, which issued as U.S. Pat. No. 9,045,779 on Jun. 2, 2015, entitled "Increased Ethanol Production by Genetic Engineering of Microorganisms to Express Hemoglobin," which is a divisional application of U.S. application Ser. No. 13/098, 189, filed on Apr. 29, 2011, which issued as U.S. Pat. No. 8,790,911, on Jul. 29, 2014, entitled "Increased Ethanol Production by Genetic Engineering of Microorganisms to Express Hemoglobin," which claims the benefit of U.S. Provisional Application Ser. No. 61/329,796, filed on Apr. 30, 2010, entitled "Increased Ethanol Production by Genetic Engineering of Bacteria to Express Hemoglobin," each of which are incorporated herein by reference in their entirety.

SEQUENCE LISTING

Incorporated by reference herein in its entirety is the Sequence Listing entitled "Sequence-Listing.txt", created Aug. 8, 2013, size of 28 kilobytes.

FIELD OF THE INVENTION

The invention relates to the fields of microbiology and genetic engineering. More specifically, the present disclosure describes that expression of a hemoglobin gene from a bacteria of the genus *Vitreoscilla* was found to increase production of fermentation products in microorganisms grown under substantially anaerobic conditions.

BACKGROUND

The following description provides a summary of information relevant to the present disclosure and is not a concession that any of the information provided or publications referenced herein is prior art to the claimed invention.

Production of fermentation products, including ethanol, by microorganisms provides an alternative energy source to fossil fuels and is therefore an important area of current research.

The pyruvate decarboxylase and alcohol dehydrogenase enzymes of *Zymomonas mobilis* provide a more efficient biochemical pathway for the production of ethanol in comparison to for example the pyruvate formate lyase pathway of *E. coli* (FIG. 14). Dien, B. S., et al. "Bacteria engineered for fuel ethanol production: current status." *Applied Microbiology and Biotechnology* 63 (2003): 258-266. The efficiency of the pyruvate decarboxylase and alcohol dehydrogenase II biochemical pathway to ethanol results at least in part from the necessary investment of only one NADH in the conversion of pyruvate to ethanol whereas other ethanol pathways such as the pyruvate formate lyase pathway require the investment of two NADH in the conversion of pyruvate to ethanol.

In the context of fermentation of the sugar xylose, ethanol production efficiency may be gained by expression of the enzyme xylose isomerase. Xylose is commonly fermented to ethanol through the intermediate xylulose-5-phosphate which is then fed into the pentose phosphate pathway. The conversion of xylose to xylulose may be a less efficient two-step conversion from xylose to xylitol then to xylulose or a more efficient one-step conversion, if xylose isomerase is present, directly from xylose to xylulose.

*Vitreoscilla* is a genus of filamentous gram-negative bacteria found in freshwater sediments, stagnant ponds, cow dung and decaying vegetable matter where oxygen availability is low. *Vitreoscilla* C1 is an obligate aerobe which synthesizes a soluble hemoglobin (VHb). VHb is a dimer of two identical subunits each having a relative mass of 15.8 kDa and a b heme. VHb is the best characterized member of the family of bacterial hemoglobin proteins.

VHb has been expressed in *Saccharomyces cerevisiae* (*S. cerevisiae*), baker's yeast, and increased ethanol production was demonstrated in comparison to non-VHb expressing controls on synthetic dextrose medium supplemented with 0.1% glucose. Chen, W., et al. "Intracellular Expression of *Vitreoscilla* Hemoglobin Alters the Aerobic Metabolism of *Saccharomyces cerevisiae*." *Biotechnology Progress* 10 (1994): 308-313. Also, the VHb expressing strain was shown to grow to a lower cell culture density indicating a redirection of carbon from biomass production to ethanol. The metabolic changes to *S. cerevisiae* were attributed to changes in respiration and addition of respiration inhibitor antimycin A was shown to eliminate the effect of VHb on ethanol production.

VHb expression has been studied in *E. coli* from an isopropyl-β-D-thiogalactopyranoside (IPTG) inducible plasmid for the resulting effects on metabolism under low oxygen conditions in 0.4% glucose supplemented complex medium. Tsai, P. et al. "Effect of *Vitreoscilla* Hemoglobin Dosage on Microaerobic *Escherichia coli* Carbon and Energy Metabolism." *Biotechnology and Bioengineering* 49 (1996): 139-150. It was found that increased concentrations of VHb (induced by increased concentrations of IPTG) increased the final cell culture density as measured by increases in the grams dry cell weight per liter. However, it was found that concentrations of ethanol were decreased monotonically with increasing VHb dosage. According to this study, VHb in *E. coli* redirected carbon away from ethanol production toward biomass production.

Most recently, VHb expression in *S. cerevisiae* was found to increase ethanol production efficiency on yeast synthetic complete media with 5% xylose. Ruohonen L., et al. "Expression of *Vitreoscilla* hemoglobin improves the metabolism of xylose in recombinant yeast *Saccharomyces cerevisiae* under low oxygen conditions." *Enzyme and Microbial Technology* 39 (2006): 6-14. In both yeast and *E. coli*, xylose is metabolized to ethanol via the pentose phosphate pathway (PPP). The wild-type yeast pathway for preparation of xylose for entry into PPP comprises a two-step reductive and oxidative conversion of xylose to xylulose requiring the enzymes xylose reductase and xylitol dehydrogenase. First xylose is reduced to xylitol by xylose reductase with NADPH→NADP+ as cofactor, and second xylitol is oxidized to xylulose by xylitol dehydrogenase with NAD+→NADH as cofactor. Inefficient xylose metabolism in yeast has been attributed in part to the redox cofactor imbalance in pre-PPP xylose preparation between the reduction of xylose, which causes NADP+ accumulation, and the oxidation of xylitol, which causes NADH accumulation. One of the consequences of this imbalance is believed to be the build-up of xylitol, as low oxygen conditions limit regeneration of NAD+. In the study by Ruohonen, VHb expression was found to reduce xylitol production by as much as 40% and increase ethanol production by as much as 30%. The primary explanation for these improvements proposed by the authors was that VHb facilitated conversion of NADH to its oxidized form, NAD+, thus driving xylose from the xylitol intermediate to xylulose and thus facilitating entry of xylose into PPP.

In contrast to wild-type yeast, wild-type *E. coli* convert xylose to xylulose in one step with the enzyme xylose isomerase. Consequently, xylose preparation for PPP in *E. coli* does not have a redox cofactor imbalance and xylitol is not an intermediate. If the primary explanation proposed by the authors of the yeast VHb expression-xylose fermentation study accounts for most of the increase in ethanol production, then it would be expected that VHb would not similarly increase ethanol production from *E. coli* xylose fermentation.

There remains a need to develop novel microorganisms and methods which can increase the efficiency of the production of fermentation products, such as ethanol.

SUMMARY

The present disclosure describes novel microorganisms and methods for producing fermentation products with such novel microorganisms. In particular, the disclosure describes novel microorganisms which utilize a carbon source to produce a fermentation product wherein said microorganism expresses a pyruvate decarboxylase gene (e.g. pdc) and at least one alcohol dehydrogenase gene (e.g. adhb) from a bacteria of the genus *Zymomonas*, and further wherein said microorganism comprises at least one genetic modification which provides for expression of a hemoglobin gene from a bacteria of the genus *Vitreoscilla*. Said microorganism is a prokaryote or eukaryote. In one embodiment, said microorganism is a prokaryote. In an embodiment, said microorganism is a bacteria of a genus selected from the group consisting of *Escherichia* and *Zymomonas*. In one embodiment, said microorganism is a bacteria of the genus *Escherichia*. In an embodiment, said microorganism is *Escherichia coli*. In another embodiment, the microorganism is a bacteria of the genus *Zymomonas*. In an embodiment, said microorganism is *Zymomonas mobilis*. Said microorganisms have improved fermentation performance compared to an essentially genetically identical microorganisms which lack at least one genetic modification which provides for expression of a hemoglobin gene from a bacteria of the genus *Vitreoscilla*. In an embodiment, the expression of a hemoglobin gene from a bacteria of the genus *Vitreoscilla* in said microorganism produces a concentration of intracellular hemoglobin greater than 0 and less than about 125 nmoles per gram wet weight of cells. In another embodiment, the expression of a hemoglobin gene from a bacteria of the genus *Vitreoscilla* in said microorganism produces a concentration of intracellular hemoglobin greater than 0 and less than about 100 nmoles per gram wet weight of cells. In an embodiment, the expression of a hemoglobin gene from a bacteria of the genus *Vitreoscilla* in said microorganism produces a concentration of intracellular hemoglobin greater than 0 and less than about 75 nmoles per gram wet weight of cells.

In addition, the present disclosure describes a method for producing a fermentation product comprising: a) providing a microorganism which utilizes a carbon source to produce a fermentation product wherein said microorganism expresses a pyruvate decarboxylase gene and at least one alcohol dehydrogenase gene from a bacteria of the genus *Zymomonas*; b) modifying the genetics of said microorganism wherein said modifying comprises at least one genetic modification which provides for expression of a hemoglobin gene from a bacteria of the genus *Vitreoscilla*; and c) contacting the genetically modified microorganism of step b) with at least one carbon source under substantially anaerobic conditions. Said microorganism of the method for producing a fermentation product is a prokaryote or eukaryote. In an embodiment, said microorganism is a prokaryote. In one embodiment, said microorganism is a bacteria of a genus selected from the group consisting of *Escherichia* and *Zymomonas*. In one embodiment, said method for producing a fermentation product wherein the fermentation product is ethanol. In an embodiment, said method for producing a fermentation product wherein the at least one carbon source is selected from the group consisting of glucose and xylose. In one embodiment, said method for producing a fermentation product wherein the expression of a hemoglobin gene from a bacteria of the genus *Vitreoscilla* produces a concentration of intracellular hemoglobin in said microorganism greater than 0 and less than about 125 nmoles per gram wet weight of cells. In an embodiment, said method for producing a fermentation product wherein the expression of a hemoglobin gene from a bacteria of the genus *Vitreoscilla* produces a concentration of intracellular hemoglobin in said microorganism greater than 0 and less than about 100 nmoles per gram wet weight of cells. In one embodiment, said method for producing a fermentation product wherein the expression of a hemoglobin gene from a bacteria of the genus *Vitreoscilla* produces a concentration of intracellular hemoglobin in said microorganism greater than 0 and less than about 75 nmoles per gram wet weight of cells.

Further, the disclosure describes a method for increasing production of a fermentation product comprising: a) providing a microorganism which utilizes a carbon source comprising xylose to produce a fermentation product wherein said microorganism expresses at least one xylose isomerase gene; b) modifying the genetics of said microorganism wherein said modifying comprises at least one genetic modification which provides for expression of a hemoglobin gene from a bacteria of the genus *Vitreoscilla*; and c) contacting the genetically modified microorganism of step b) with at least one carbon source comprising xylose under substantially anaerobic conditions wherein production of the fermentation product is increased compared to fermentation under equivalent conditions with an essentially genetically identical microorganism which lacks at least one genetic modification which provides for expression of a hemoglobin gene from a bacteria of the genus *Vitreoscilla*. In one embodiment, said method for increasing production of a fermentation product wherein the fermentation product is ethanol. Said microorganism of the method for increasing production of a fermentation product is a prokaryote or eukaryote. In an embodiment, said microorganism is a prokaryote. In an embodiment, said microorganism is a bacteria of the genus *Escherichia*. In one embodiment, said method for increasing production of a fermentation product wherein the expression of a hemoglobin gene from a bacteria of the genus *Vitreoscilla* produces a concentration of intracellular hemoglobin in said microorganism greater than 0 and less than about 125 nmoles per gram wet weight of cells. In an embodiment, said method for increasing production of a fermentation product wherein the expression of a hemoglobin gene from a bacteria of the genus *Vitreoscilla* produces a concentration of intracellular hemoglobin in said microorganism greater than 0 and less than about 100 nmoles per gram wet weight of cells. In one embodiment, said method for increasing production of a fermentation product wherein the expression of a hemoglobin gene from a bacteria of the genus *Vitreoscilla* produces a concentration of intracellular hemoglobin in said microorganism greater than 0 and less than about 75 nmoles per gram wet weight of cells. In an embodiment, said method for increasing production of a fermentation product wherein the carbon source is derived from cellulosic biomass.

In one embodiment, the present disclosure describes microorganisms which are bacteria of the genus *Escherichia* wherein the genes pyruvate decarboxylase (pdc) and alcohol dehydrogenase II (adhb) from a bacteria of the genus *Zymomonas* are heterologously expressed in the microorganisms. The expression of pdc and adhb is provided by insertion of one or both of such genes into the chromosome of the bacteria of the genus *Escherichia* or is provided for by presence of one or both such genes on an plasmid. The expression of a hemoglobin gene from a bacteria of the genus *Vitreoscilla* is provided by insertion of such hemoglobin gene into the chromosome of the bacteria of the genus *Escherichia*, is provided for on an plasmid which is the same plasmid carrying pdc and/or adhb or is provided on a plasmid which does not carry either pdc or adhb.

In another embodiment, the present disclosure describes the microorganism is a bacteria of the genus *Zymomonas* which has endogenous expression of at least one pyruvate decarboxylase and at least one alcohol dehydrogenase gene wherein a hemoglobin gene from a bacteria of the genus *Vitreoscilla* is provided by insertion of such hemoglobin gene into the chromosome of such microorganism or is provided on a plasmid.

In another embodiment, the present disclosure describes a microorganism which utilizes a carbon source comprising xylose to produce a fermentation product wherein said microorganism expresses a xylose isomerase enzyme and said microorganism is genetically modified such that a hemoglobin gene from a bacteria of the genus *Vitreoscilla* is provided by insertion of such hemoglobin gene into the chromosome of such microorganism or is provided on a plasmid. The xylose isomerase gene may be endogenously expressed or heterologously expressed. The xylose isomerase gene may be a wild-type gene, a mutated gene or a purposefully modified gene. In one embodiment, said microorganism produces a concentration of intracellular hemoglobin greater than 0 and less than about 125 nmoles per gram wet weight of cells. In an embodiment, said microorganism produces a concentration of intracellular hemoglobin greater than 0 and less than about 100 nmoles per gram wet weight of cells. In one embodiment, said microorganism produces a concentration of intracellular hemoglobin or greater than 0 and less than about 75 nmoles per gram wet weight of cells.

BRIEF DESCRIPTION OF THE FIGURES

FIG. 5 illustrates a gel confirming development of novel *E. coli* strain FBR5/pTS4 with two stable plasmids: (1) pLOI297 (which carries pdc and adhb) and (2) pTS4. DNA from each clone was separately PCR amplified for pdc+adhb in one reaction and vgb+TcR in another reaction. PCR products for each clone were combined.

FIG. 6 illustrates a gel confirming development of novel *E. coli* strain FBR5/pTS5 (pdc, adhb and vgb all on one plasmid) by restriction endonuclease digestion with XhoI, BamHI, and PstI as well as PCR of the *Vitreoscilla* hemoglobin gene (vgb) and pyruvate decarboxylase (pdc)+alcohol dehydrogenase B (adhb) cassette.

DETAILED DESCRIPTION

Figure 1:
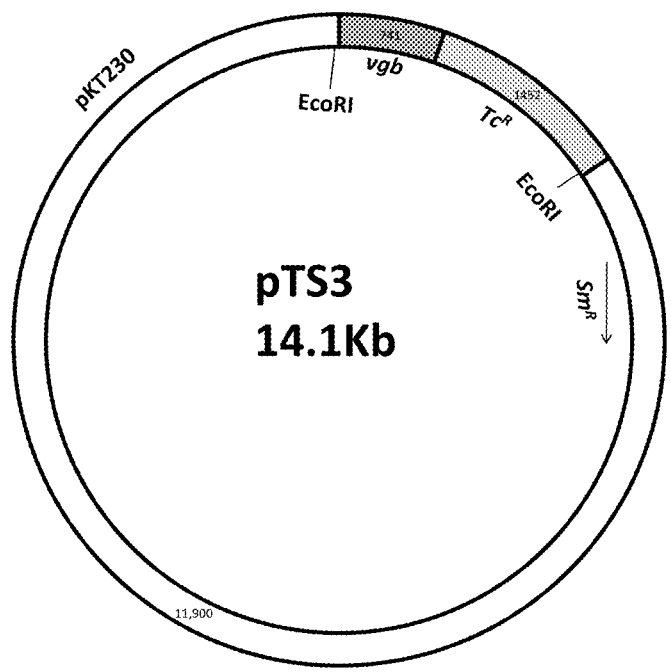
FIG. 1 illustrates a diagram of novel plasmid pTS3 which carries the *Vitreoscilla* hemoglobin gene (vgb) on a broad host range, relatively low copy number plasmid (in comparison to for example pUC plasmids), pKT230.

The practice of the invention disclosed herein employs, unless otherwise indicated, conventional methods of microbiology, molecular biology, and recombinant DNA techniques within the level of skill in the art. Such techniques are explained fully in the literature. See, e.g., (Sambrook, J., and D. W. Russell. *Molecular Cloning: A Laboratory Manual.* 3$^{rd}$ ed. Cold Spring Harbor, New York: Cold Spring Harbor Laboratory Press, 2001.

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

As used in this specification, including the appended claims, the singular forms "a," "an," and "the" include plural references, unless the content clearly dictates otherwise, and are used interchangeably with "at least one" and "one or more."

As used herein, the term "about" represents an insignificant modification or variation of the numerical values such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, the term "gene" refers to a nucleic acid fragment that expresses a specific protein, which may include regulatory sequences preceding (5' non-coding sequences) and following (3' non-coding sequences) the coding sequence.

As used herein, the term "expression" refers to the transcription and stable accumulation of sense (mRNA) or antisense RNA derived from a gene. Expression may also refer to translation of mRNA into a polypeptide.

As used herein, the term "fermentation product" includes for instance ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxypropionic acid, glyconic acid, tartaric acid and amino acids such as L-glutaric acid, L-lysine, L-aspartic acid, L-tryptophan, L-arylglycines or salts of any of these acids.

As used herein, the term "microorganism" has its conventional meaning in the art and includes bacteria, protozoa, yeasts, molds, and viruses.

As used herein, the term "substantially anaerobic" or "microaerobic" has its conventional meaning in the art and includes low oxygen conditions under which fermentative metabolism is favored over aerobic metabolism.

As used herein, the term "substantially genetically identical" refers to a level of genetic identity greater than about 95%.

As used herein, the term "carbon source" has its conventional meaning in the art and includes a nutrient comprising at least one carbon molecule. Examples include but are not limited to glucose, xylose, galactose, fructose, mannose, arabinose, and the like.

As used herein, the term "messenger RNA (mRNA)" refers to the RNA that is without introns and that can be translated into protein by the cell.

As used herein, the term "genetic modification" refers to the introduction of one or more heterologous nucleic acid sequences into one or more cells, to provide for expression of a gene or protein of interest.

As used here, the term "transformation", refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms as well as "transformants".

As used herein, the terms "plasmid" and "vector", refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term "lignocellulosic" refers to a composition comprising both lignin and cellulose. Lignocellulosic material may also comprise hemicellulose.

As used herein, the term "cellulosic" refers to a composition comprising cellulose and additional components, including hemicellulose.

As used herein, the term "biomass" refers to any cellulosic or lignocellulosic material and includes materials comprising cellulose, and optionally further comprising hemicellulose, lignin, starch, polysaccharides, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover or fiber, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

This disclosure describes increased fermentation product production in general, and increased ethanol production in particular, from fermentation of a carbon source, such as glucose or xylose, by genetically engineering ethanol producing microorganisms to express a hemoglobin from a bacteria of the genus *Vitreoscilla*.

Figure 14:
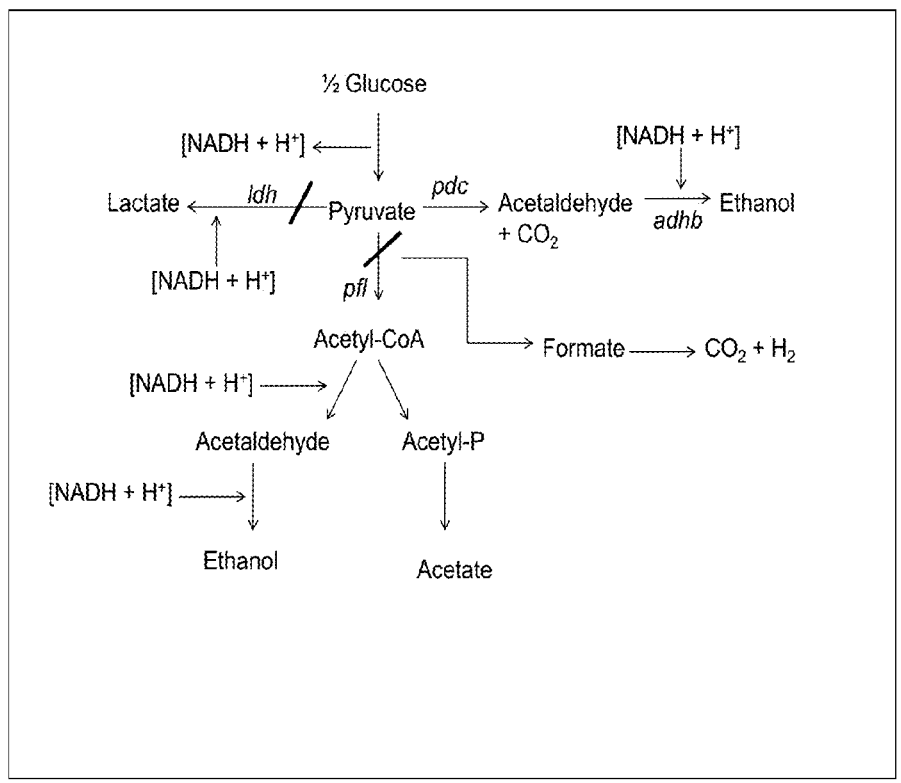
FIG. 14 illustrates the microaerobic pathways knocked out in E. coli strain NZN111 causing NZN111 to be unable to grow microaerobically because the lactate dehydrogenase (ldh) and pyruvate formate lyase (pfl) enzymes have been knocked out resulting in inability to reduce pyruvate via fermentation and regenerate NAD$^+$. Heavy bars indicate knock out of pathway.

In one embodiment, *E. coli* strain FBR5 was genetically engineered to express *Vitreoscilla* hemoglobin (VHb). FBR5 is an industrially significant ethanol producing *E. coli* strain because it harbors plasmid pLOI297 (FBR5 is *E. coli* strain NZN111 plus pLOI297) with the pdc and adhb of *Z. mobilis*, providing a more efficient ethanol pathway, as well as having knockouts of ldh (gene for lactate dehydrogenase) and pfl (gene for pyruvate formate lyase), impeding formation of the undesirable fermentation products lactate and acetate (FIG. 14). The VHb gene, vgb, was maintained under the control of the native oxygen sensitive *Vitreoscilla* promoter and pdc and adhb were both under control of the lac promoter.

Three novel strains of *E. coli* were developed to test the effects of VHb on ethanol production.

In two of the strains, vgb was expressed on a second plasmid, in addition to pLOI297. The plasmid of FBR5, pLOI297, carrying pdc and adhb is a pUC18 based plasmid. Ingram, L. O., et al. "Genetic Engineering of Ethanol Production in *Escherichia coli*." *Applied and Environmental Microbiology* 53.10 (1987): 2420-2425. pUC based plasmids are derived from ColE1 plasmids and have negative feedback control of replication initiation and thus incompatibility with other ColE1 plasmids. Consequently, it is generally not possible to stably propagate two plasmids of the same incompatibility group (e.g. two pUC plasmids) in the same cell. However, plasmids from different incompatibility groups, i.e. having different origins of replication, can stably propagate in the same cell. Lengeler, J. W., et al. *Biology of the Prokaryotes*. New York, N.Y.: Blackwell Science, 1999.

Thus, the ability of plasmids from different incompatibility groups to co-exist within the same cell was used to develop two of the three novel *E. coli* strains. Strain FBR5/pTS3 was developed by introduction of novel plasmid pTS3 (FIG. 1) into strain FBR5 while preventing the rejection of plasmid pLOI297. Plasmid pTS3 was constructed by inserting the *Vitreoscilla* hemoglobin gene, vgb, into plasmid pKT230. Plasmid pKT230 has two origins of replication each of which is in a different incompatibility group than ColE1 plasmids. Bagdasarian M., et al. "Specific-purpose plasmid cloning vectors: II. Broad host range, high copy number, RSF1010-derived vectors, and a host vector system for gene cloning in *Pseudomonas*." *Gene* 16 (1981): 237-247. pKT230 is composed of plasmid pACYC177 ligated with plasmid RSF1010. RSF1010 belongs to the IncQ incompatibility group and pACYC177 contains the replication system of miniplasmid P15A. Chang, A. C. Y. and Cohen, S. N., "Construction and Characterization of Amplifiable Multicopy DNA Cloning Vehicles Derived from P15A Cryptic Miniplasmid." *Journal of Bacteriology* 134.3 (1978): 1141-1156.

Strain FBR5/pTS4 was developed by introduction of novel plasmid pTS4 (FIG. 2) into strain FBR5 together with pLOI297. Plasmid pTS4 was constructed by insertion of vgb into plasmid pBBR1MCS-5. Plasmid pBBR1MCS-5 has an origin of replication that is compatible with ColE1 plasmids. Kovach, M. E., et al. "Four new derivatives of the broad-host-range cloning vector pBBR1MCS carrying different antibiotic-resistance cassettes." *Gene* 166 (1995): 175-176.

The third novel *E. coli* strain was developed by combining all three genes of interest, pdc, adhb and vgb, into one novel plasmid (pTS5), curing FBR5 of the pLOI297 plasmid to produce strain NZN111 and introducing pTS5 into strain NZN111.

After the three novel ethanol producing strains were developed: (1) FBR5/pTS3, (2) FBR5/pTS4 and (3) NZN111/pTS5, the cell physiology of these strains was studied. Data collection focused on *Vitreoscilla* hemoglobin (VHb) production and ethanol production under different growth conditions.

The VHb expression level of FBR5/pTS3, the lowest VHb expression of the novel strains, was approximately twice the normal induced level in *Vitreoscilla*. Geckil, H., et al. "Enhanced production of acetoin and butanediol in recombinant *Enterobacter aerogens* carrying *Vitreoscilla* hemoglobin gene." *Bioprocess and Biosystem Engineering* 26 (2004): 325-330. Of the three novel strains, only NZN111/pTS5 expressed VHb at levels as high as those commonly seen for plasmids in *E. coli* with the VHb gene, vgb, controlled by the native promoter and FBR5/pTS4 expressed VHb at about half of commonly seen levels. Dikshit, K. L., D. A. Webster. "Cloning, characterization and expression of the bacterial globin gene from *Vitreoscilla* in *Escherichia coli*." *Gene* 70 (1988): 377-386. Fish, P. A, et al., "*Vitreoscilla* hemoglobin enhances the first step in 2,4-dinitrotoluene degradation in vitro and at low aeration in vivo." *Journal of Molecular Catalysis B: Enzymatic* 9 (2000): 75-82.

Figure 8:
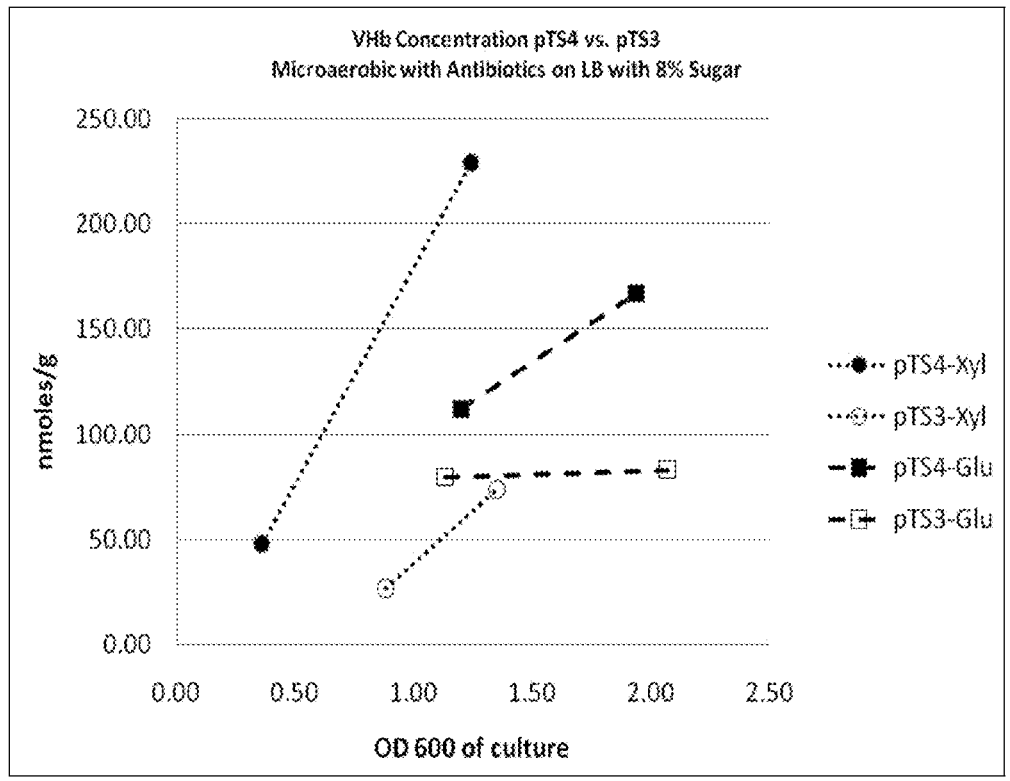
FIG. 8 illustrates a graph which provides data from carbon monoxide difference spectra which indicated that under microaerobic conditions with antibiotics that ethanol producing *E. coli* expressing VHb, FBR5/pTS3 and FBR5/pTS4, produced different concentrations of VHb on phosphate buffered LB enriched with 8% (w/v) sugar; measured in nmoles VHb/g wet weight of cells.

In the study by Tsai et al. 1996, where VHb expression in *E. coli* from an IPTG inducible plasmid under microaerobic conditions was found to reduce ethanol production monotonically with increasing VHb concentrations including the lowest VHb concentration tested. The lowest VHb expression level tested was 500 nmoles/gram dry cell weight or approximately 125 nmoles/gram wet cell weight. Tsai, P. S., et al. "Effect of *Vitreoscilla* Hemoglobin Dosage on Microaerobic *Escherichia coli* Carbon and Energy Metabolism." *Biotechnology and Bioengineering* 49 (1996): 139-150. This expression level was comparable to the expression level of FBR5/pTS4 under microaerobic conditions while the expression level of FBR5/pTS3 under microaerobic conditions was approximately half of the lowest level of VHb expression tested by Tsai et al. (FIG. 8).

Thus, the study of Tsai et al. teaches away from VHb expression for increased ethanol production, particularly in *E. coli* which produce ethanol with the wild-type ethanol pathway. However, it has been surprisingly found that lower levels of VHb expression than those tested by Tsai et al. actually increase ethanol production.

The results indicate that a relatively low level of VHb expression is beneficial to ethanol production, even under the selective pressure of additional antibiotics and even at the metabolic cost of maintaining additional plasmid DNA. For example, FBR5/pTS3 produced 15% higher ethanol concentration (v/v) on buffered LB enriched with 8% (w/v) glucose under microaerobic conditions with antibiotics and 119-138% higher ethanol concentration (v/v) on buffered LB enriched with 8% (w/v) xylose under microaerobic conditions without antibiotics.

EXAMPLES

The following examples are provided for illustrative purposes only and are not intended to limit the scope of the invention as defined in the appended claims.

Example 1

Development of Novel Strains Expressing a Pyruvate Decarboxylase and a Alcohol Dehydrogenase from a Bacteria of the Genus *Zymomonas*; a Xylose Isomerase Enzyme; and a Hemoglobin Gene from a Bacteria of the Genus *Vitreoscilla*

A. Cloning Methods Utilized

Polymerase chain reactions were separately performed using two polymerase mixtures. For cloning purposes, TcR (tetracycline resistance) was PCR amplified from plasmid pBR322 using JumpStart ReadyMix Taq (Sigma-Aldrich Catalog #P2893). Taq ReadyMix was also used for diagnostic purposes to detect for the presence of particular plasmid or gene in cells. All other PCR amplification for cloning was performed with the Phusion High-Fidelity PCR Kit (New England BioLabs Catalog #F-5535).

All primers for PCR amplification were obtained from Integrated DNA Technologies (Coralville, Iowa) and the following primers were used for each amplification: (1) vgb with PstI ends was PCR amplified from pUC8:16 Primer 1—(SEQ ID NO: 11) 5'-AAA CTG CAG GTT AAA AGT ATT TGA GTT TTG ATG TGG A-3' and Primer 2—(SEQ ID NO: 12) 5'-CCA ATG CAT TGG TTC TGC AGG TGT AAA TAT CAG ACG TAA AAA GAC CA-3'; (2) TcR with EcoRI ends was PCR amplified from pBR322 using Primer 1—(SEQ ID NO: 13) 5'-AAA ACT GCA GAA AAC CCG GGC TCT TCC TTT TTC AAT ATT ATT GAA GCA-3' and Primer 2—(SEQ ID NO: 14) 5'-TGC ATT GGC TGC AGT TTC CCG GGT TTT TGA ATT CAT ATG TTC TGC CAA GGG TTG GTT TG-3'; (3) TcR with HindIII ends and point mutation was PCR amplified from pBR322 using Primer 1—(SEQ ID NO: 15) 5'-CCC AAG CTT TTG ACA GCT TAT CAT CGA TAA GCT ATA ATG CGG TAG TTT ATC AC-3' and Primer 2—(SEQ ID NO: 16) 5'-CCC AAG CTT ATA TGT TCT GCC AAG GGT TGG TTT G-3'; (4) vgb+TcR cassette with EcoRI ends was PCR amplified from pTS2 using Primer 1—(SEQ ID NO: 17) 5'-GGC GAA TTC CTG CAA GGC GAT TAA GTT GG-3' and Primer 2—(SEQ ID NO: 18) 5'-GGC GAA TTC CAA GGC ACA CCT GAA GAC G-3'; (5) pdc+adhb cassette with BamHI ends was PCR amplified from pLOI297 using Primer 1—(SEQ ID NO: 19) 5'-AAA GGA TCC GCG CAA CGT AAT TAA TGT GAG TT-3' and Primer 2—(SEQ ID NO: 20) 5'-TTT GGA TCC CCA AAT GGC AAA TTA TT-3'; and (6) vgb+TcR cassette with XhoI ends was PCR amplified from pTS2 using Primer 1—(SEQ ID NO: 21) 5'-GGC CTC GAG CTG CAA GGC GAT TAA GTT GG-3' and Primer 2—(SEQ ID NO: 22) 5'-GGC CTC GAG CAA GGC ACA CCT GAA GAC G-3'.

PCR amplification cycles were the following: (1) vgb with PstI ends PCR amplified from pUC8:16 [step 1—94° C. for 5 minutes, step 2—94° C. for 30 seconds, step 3—59° C. for 30 seconds, step 4—72° C. for 1 minute and 15 seconds, step 5—72° C. for 5 minutes and step 6—held at 4° C.; amplification cycle (steps 2-4) repeated 30 times]; (2) TcR with EcoRI ends was PCR amplified from pBR322 using the same cycle as for vgb with PstI ends, including annealing temperature, except elongation step 4—72° C. for 2 minutes; (3) TcR with HindIII ends and point mutation was PCR amplified from pBR322 again using the same cycle for vgb with PstI ends, except a temperature gradient for annealing temperatures was used between 57.7° C. and 61.6° C. where all temperatures worked and elongation step 4—72° C. for 2 minutes (4) vgb+TcR cassette with EcoRI ends was PCR amplified from pTS2 using Phusion polymerase [step 1—98° C. for 30 seconds, step 2—98° C. for 10 seconds, step 3—55° C. for 30 seconds, step 4—72° C. for 1 minute and 30 seconds, step 5—72° C. for 5 minutes and step 6—held at 4° C.; amplification cycle (steps 2-4) repeated 35 times]; (5) pdc+adhb cassette with BamHI ends was PCR amplified from pLOI297 using Phusion polymerase and the same cycle as amplicon 4 except a temperature gradient for annealing temperatures was used between 50° C. and 70° C. where all temperatures worked and elongation step 4—72° C. for 2 minutes; and (6) vgb+TcR cassette with XhoI ends was PCR amplified from pTS2 using Phusion polymerase and same cycle as for the vgb+TcR cassette with EcoRI ends.

All PCR reactions were run in a MJ Research PTC-200 Peltier Thermal Cycler. Excluding use of the PCR-Script Amp system, before enzymatic digestion, all PCR products were cleaned with QIAquick PCR Purification kit (Qiagen Catalog #28104).

DNA gel electrophoresis was done using 1% agarose gels (35 ml of either 1×TAE or 0.5×TBE buffer prepared as described in Sambrook 2001 (Sambrook, J., and D. W. Russell. *Molecular Cloning: A Laboratory Manual.* 3$^{rd}$ ed. Cold Spring Harbor, New York: Cold Spring Harbor Laboratory Press, 2001) and 0.35 g of electrophoresis grade agarose (Amresco Catalog #0710-500G) with 1:10,000 dilution of gel stain GelRed (Biotium Catalog #41003). Agarose weights were measured using a Denver Instruments APX-60 balance. Gels were run in a horizontal gel box (similar to an Owl Separation Systems Model B1) with a power supply (VWR Scientific Model VWR 105) set at 130 V. All ladders used were HindIII restriction endonuclease digestions of λ-DNA.

All endonuclease digestions were performed using New England BioLabs enzymes and buffers. Reactions were incubated in an incubator (VWR Scientific Model VWR1530) at 37° C. for a minimum of 1 hour to as long as overnight.

For all ligation reactions, except the cloning of pTS1 and pTS3, all digested DNA was extracted from gels before preparation of ligation reactions. For pTS3, the insert was gel extracted, but pKT230 was too large (12 kb) to gel extract because it could not be removed from beads due to excessively tight binding. All gel extractions were performed using the Qiaex II system (Qiagen Catalog #20021). The sole deviation from the standard protocol was that DNA was heated to 60° C. for ten minutes in order to elute from beads.

All ligations, other than PCR-Script Amp ligations, were incubated overnight at between 4° C. and 16° C. using T4 DNA ligase from New England BioLabs (Catalog #M0202S). Total concentration of DNA in ligations (vector+insert) was approximately 10 ng/μl, generally 100 ng in 10 μl ligation reactions. Insert to plasmid molar ratios were approximately 7:1.

Plasmids were prepped according to three primary protocols (1) Qiagen QIAprep Spin Miniprep Kit (Catalog #27104), (2) Promega PureYield Plasmid Midiprep System (Catalog #A2492) and (3) alkaline lysis (Sambrook 2001).

For pTS3, pTS4 and pTS5, PCR products were prepared for insertion by ligation into intermediate plasmid PCR-Script Amp. The Stratagene PCR-Script Amp cloning kit (Catalog #211188) was used. All reactions were performed at half volume to extend kit life. Also the competent cells provided by the kit were not used because they were found to exhibit a high degree of tetracycline antibiotic resistance.

Chemical competent and electro-competent cells were prepared according to the protocol of Sambrook 2001. It was found that electrocompetent cells had a very short shelf-life at −80° C. NEB 5-alpha electrocompetent *E. coli* were used for several transformations and found to have a much longer shelf life at −80° C. (New England Biolabs Catalog #C2989K).

All heat shock transformations were carried out as described in Sambrook 2001. When tetracycline selection was used, heat shock was the necessary procedure because electroporation has low efficiency. Steele, C., S. Zhang, and E. J. Shillitoe. "Effect of Different Antibiotics on Efficiency of Transformation of Bacteria by Electroporation." BioTechniques 17.2 (1994): 360-365. Electroporation was done using a BTX Electro Square Porator ECM830 and BTX 1 mm gap cuvettes. The settings used were 500 V and pulse length of 17 ms.

Working antibiotic concentrations for ampicillin (Amp), kanamycin (Km), streptomycin (Sm), gentamicin (Gm) and tetracycline (Tc) were 100 μg/ml, 50 μg/ml, 50 μg/ml, 5 μg/ml and 25 μg/ml, respectively, throughout the experiments. Stock solutions were prepared in sterile dH2O of (1) Amp-sodium salt of 25 mg/ml, (2) Km 10 mg/ml, (3) Sm-sulfate 10 mg/ml, and Gm 10 mg/ml. The stock solution for Tc was 5 mg/ml in 50% dH2O and 50% EtOH.

All plates used for FBR5 and derivative strains had LB, appropriate antibiotics and were supplemented with 8% (w/v) xylose (D-xylose Sigma-Aldrich X1500). Selection and maintenance plates were used as follows: FBR5 on LB/Amp, FBR5/pTS3 on LB/Amp/Sm, FBR5/pTS4 on LB/Amp/Gm, NZN111 on LB/Km, pTS5/NZN111 on LB/Amp and both DH5α/pTS1 and DH5α/pTS2 on LB/Tc.

Blue white screening for β-galactosidase activity was done on LB/antibiotic plates to which 100 μl pool of LB had been added and into which 100 μl of 2% X-gal (in dimethylformamide) and 100 μl of 10 mM IPTG (in sterile dH2O) were added. This mixture was distributed evenly across the surface of the plate and allowed to soak into plates for 30 minutes.

B. Development of Novel Plasmids and Novel Strains

A strategy was developed to clone TcR (tetracycline resistance gene) from plasmid pBR322 into the HindIII site of vgb containing plasmid pUC8:16 (HindIII sites lies adjacent to vgb). The primary challenge encountered was that a HindIII site existed in the −10 sequence of the promoter of TcR of pBR322. In response, primers were designed to amplify TcR with a one base pair mismatch creating a point mutation to knockout the HindIII site and enhance the −10 sequence of the promoter by changing it from TTTAAT to the consensus sequence TATAAT. The point mutation by primer mismatch PCR was successful. The insert was ligated into pUC8:16 to create pTS2. Construction of pTS2 was confirmed by HindIII digestion, by EcoRI digestion, and PCR amplification of the insert.

A PCR strategy was developed to amplify the region of pTS2 containing vgb and TcR as one amplicon. The vgb+TcR cassette was successfully amplified with the Phusion polymerase. The vgb+TcR cassette was then successfully ligated into the intermediate cloning vector PCR-Script Amp.

Figure 2:
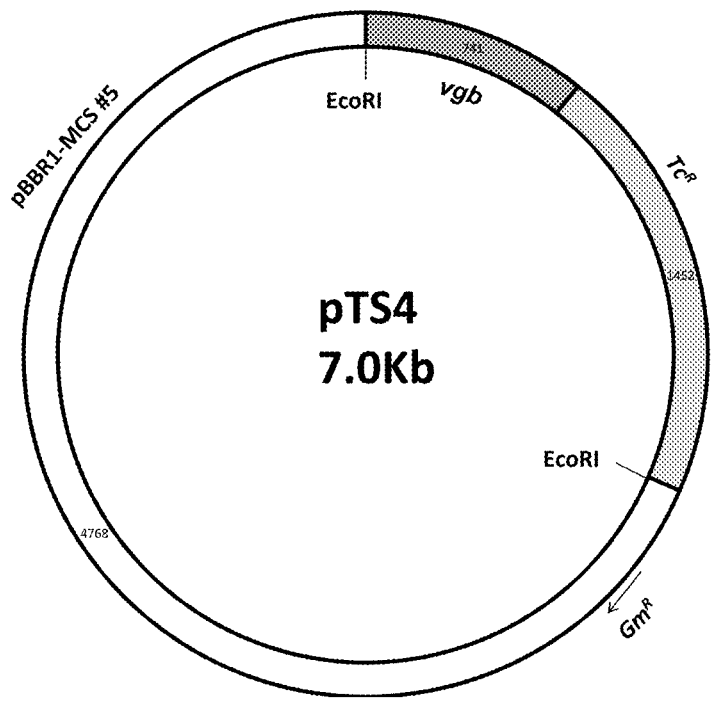
FIG. 2 illustrates a diagram of novel plasmid pTS4 which carries the *Vitreoscilla* hemoglobin gene (vgb) on a broad host range plasmid, pBBR1-MCS #5.

The vgb+TcR cassette was digested from plasmid PCR-Script Amp+vgb+TcR and inserted into the EcoRI site of pKT230 to create pTS3 (FIG. 1), and similarly inserted into the EcoRI site of pBBR1-MCS-5 to create pTS4 (FIG. 2). Construction of plasmids pTS3 and pTS4 was confirmed by EcoRI digestion, and further confirmed by PCR amplification of the insert.

Next, pTS3 and pTS4 were separately introduced into strain FBR5 by electroporation to generate strains FBR5/pTS3 and FBR5/pTS4. After electroporation, FBR5/pTS3 transformants were selected on plates of xylose enriched LB media with ampicillin and streptomycin. The presence of the two plasmids within the cells allowed for growth because pLOI297 alone conferred antibiotic resistance to ampicillin and pTS3 alone conferred resistance to streptomycin. After electroporation, FBR5/pTS4 transformants were selected on plates of xylose enriched LB media with ampicillin and gentamicin. The presence of the two plasmids within the cells allowed for growth because pLOI297 alone conferred antibiotic resistance to ampicillin and pTS4 alone conferred resistance to gentamicin.

Figure 4:
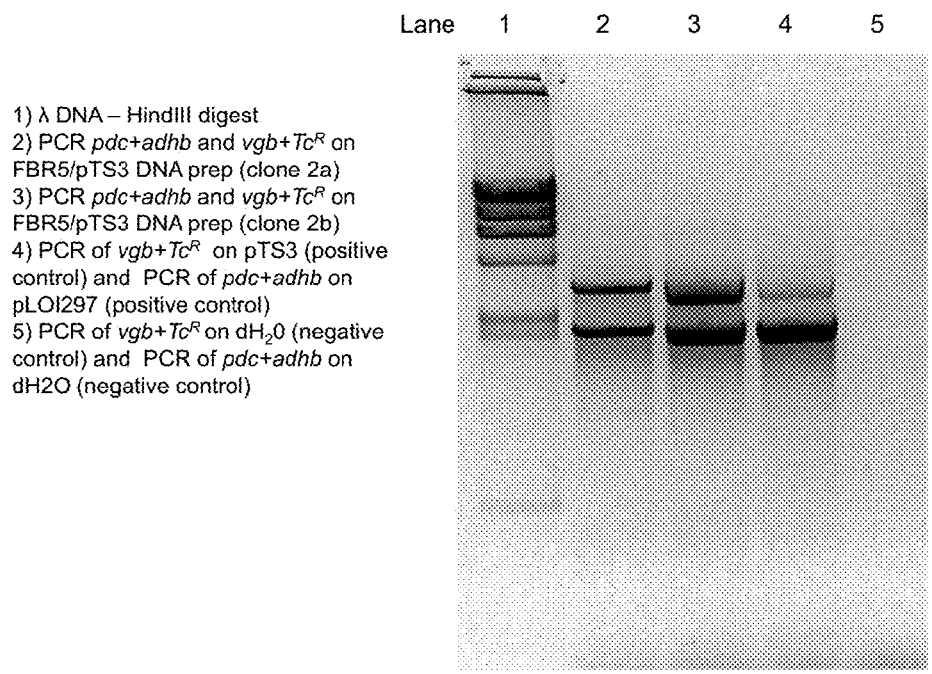
FIG. 4 illustrates a gel confirming development of novel *E. coli* strain FBR5/pTS3 with two stable plasmids: (1) pLOI297 (which carries pdc and adhb) and (2) pTS3. DNA from each clone was separately PCR amplified for pdc+adhb in one reaction and vgb+TcR in another reaction (tetracycline resistance was used to select for clones with vgb). PCR products for each clone were combined.

Development of the novel strains (FBR5/pTS3 and FBR5/pTS4) was confirmed by PCR amplification of pdc+adhb from pLOI297 in one reaction and vgb+TcR on pTS3 or pTS4 in another reaction (FIGS. 4 and 5).

Figure 3:
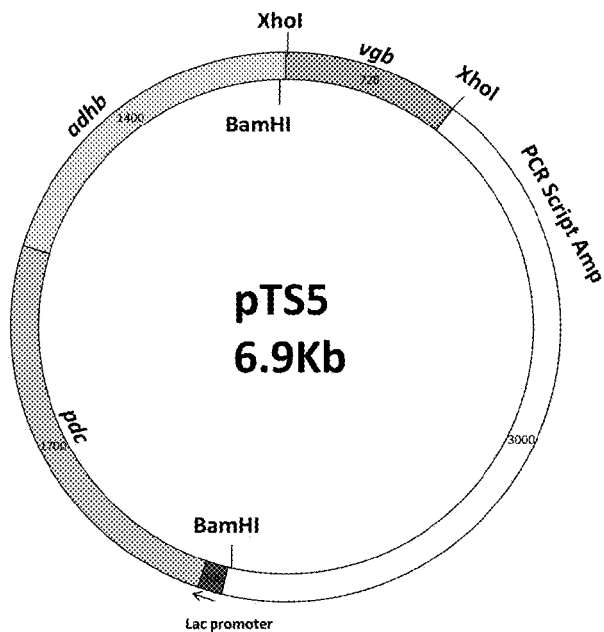
FIG. 3 illustrates a diagram of novel plasmid pTS5 which carries the pyruvate decarboxylase (pdc) and alcohol dehydrogenase II (adhb) genes from *Zymomonas mobilis* and the *Vitreoscilla* hemoglobin gene (vgb).

In order to potentially increase ethanol production efficiency by combining all three genes of interest, vgb, pdc and adhb, on one high-copy-number plasmid and to simplify growth conditions by reducing the number of antibiotics required for plasmid stabilization, pTS5 was constructed (FIG. 3).

The first step in the construction of pTS5 was use of a strategy to PCR amplify pdc and adhb together as a cassette including the lac promoter. The pdc+adhb cassette was successfully amplified with the Phusion polymerase. The pdc+adhb cassette (3.2 kb) was then successfully ligated into cloning vector PCR-Script Amp (3 kb) using blue-white screening. Previous use of the vgb+TcR cassette with EcoRI ends was not applicable for construction of pTS5 because an EcoRI restriction site was present between the lac promoter and pdc and adhb. There was no restriction site for XhoI present in the pdc+adhb cassette or within the vgb+TcR cassette, but a unique XhoI site was present on the plasmid PCR-Script Amp. Therefore, the vgb+TcR cassette was PCR amplified with XhoI ends.

Insertion of the vgb+TcR cassette with XhoI ends into cloning vector PCR-Script Amp was complicated by the occurrence of an internal deletion in TcR. It remains unknown why the vgb+TcR cassette with XhoI ends exhibited internal deletion when the vgb+TcR cassette with EcoRI ends did not. Yet, by use of blue-white screening construction of PCR-Script Amp+insert of partial vgb+TcR cassette was confirmed by digestion with restriction endonuclease XhoI, and by PCR amplification of the insert using primers specific to the vgb+TcR cassette. For clones #3 and #6, it was determined by PCR amplification with primers specific to vgb that the internal deletion in the vgb+TcR cassette was within the region of TcR and that vgb including its native oxygen sensitive promoter was intact.

Subsequently, vgb with XhoI ends was released from PCR-Script Amp vgb by restriction endonuclease digestion with XhoI and inserted into the unique XhoI site of PCR-Script Amp pdc+adhb to create novel plasmid pTS5. Selection for successful construction was difficult because the blue-white screen had been expended in generation of PCR-Script Amp pdc+adhb and the insert carried no antibiotic resistance. Ligation was performed with a molar ratio between insert and plasmid much higher that 7:1 used in previous ligations, risking multiple inserts while reducing the probably of plasmid self ligation. The ligation mixture was electroporated into NEB 5-alpha cells and plated to LB/ampicillin. All colonies were picked and used to inoculate 2 ml LB/ampicillin cultures grown overnight. 1.5 ml of each culture was pelleted and pellets were visually examined to distinguish pink color that might be attributed to VHb. Promising pellets were mini-prepped and tested for presence of PCR-Script Amp pdc+adhb+vgb (pTS5) with single cut restriction endonuclease digestion with PstI and vgb insert releasing digestion with XhoI, and further with BamHI. Construction of pTS5 was further verified by PCR amplification of pdc+adhb in one reaction and vgb in another reaction.

In order to generate novel *E. coli* strain NZN111/pTS5, FBR5 had to first be cured of plasmid pLOI297. FBR5 was repeatedly restreaked on xylose enriched LB/kanamycin plates because the kanamycin resistance gene was present on the genomic DNA where it had been used to knock out the lactate dehydrogenase gene. After repeated restreaks, FBR5 was found to have lost ampicillin resistance indicating that it had been cured of plasmid pLOI297 generating the underlying parent strain of FBR5, NZN111. NZN111 was cultured and prepared for electroporation and pTS5 was introduced by electroporation. NZN111/pTS5 transformants were screened on xylose enriched LB/ampicillin plates. Generation of novel *E. coli* strain NZN111/pTS5 was verified by restriction endonuclease digestion with XhoI, BamHI, and PstI as well as PCR amplification with primers to pdc+adhb in one reaction and primers to vgb in another reaction (FIG. 6).

Example 2

VHb Expression and Ethanol Production Studies of Novel Strains

A. Methods for Measurement of Ethanol Production, Methods for Measurement of VHb Expression, Strain Maintenance, and Statistical Tests Fermentation studies were performed with the following media: phosphate buffered LB enriched with 8% (w/v) of one of D-xylose or D-glucose. All sugar percentages herein are in percent (w/v) unless otherwise specified. Carbon monoxide difference spectra, measuring VHb expression, were collected for FBR5, FBR5/pTS3, FBR5/pTS4 and NZN111/pTS5 cultured in phosphate buffered LB enriched with 8% (w/v) xylose or 8% (w/v) glucose.

For making buffered LB the following stock solutions were prepared: (1) 40% (w/v) sugar solution in $dH_2O$ of D-xylose or D-glucose (the sugar was autoclaved separately); (2) 2×LB with no NaCl made by dissolving 10 g tryptone and 5 g yeast extract in 500 ml $dH_2O$ and autoclaving; (3) phosphate buffer, pH 7.0, by dissolving 10.8 g sodium phosphate monobasic, monohydrate and 17.3 g of sodium phosphate dibasic in 200 ml $dH_2O$ and autoclaving, and (4) sodium acetate 10% (w/v) in $dH_2O$ (also autoclaved).

The buffered and enriched LB was prepared as phosphate buffered: phosphate buffered included 50 ml 2×LB, 20 ml phosphate buffer, 20 ml of sugar stock, 9 ml $dH_2O$ and 1 ml sodium acetate.

Stock solutions of antibiotics were prepared in sterile $dH_2O$ of (1) ampicillin (Amp), 25 mg/ml, (2) kanamycin (Km), 10 mg/ml, (3) streptomycin (Sm), 10 mg/ml, and gentamicin (Gm), 10 mg/ml. Working antibiotic concentrations were 100 µg/ml Amp for FBR5 cultures, 100 µg/ml Amp and 50 µg/ml Sm for FBR5/pTS3 cultures, 100 µg/ml Amp and 5 µg/ml Gm for FBR5/pTS4 cultures and 100 µg/ml Amp for NZN111/pTS5 cultures.

All strains were maintained on LB plates with the appropriate antibiotic(s) enriched with 8% xylose. The plates were made by substituting 20% of the volume of $dH_2O$ with xylose in $dH_2O$ (40% w/v). All liquid cultures were started from single colonies as small pre-cultures of approximately 2 ml in LB with the appropriate antibiotic(s) enriched with 8% xylose. Pre-cultures were grown to stationary phase and optical densities were measured. Larger cultures were started with approximately 500 µl of pre-culture, but inoculation volumes were adjusted, taking into account optical density, to equalize biomass of inoculums across cultures.

Each aerobic culture (for VHb expression measurements) was grown as 50 ml of culture in a 250 ml Erlenmeyer flask. The media composition of the aerobic cultures was identical to the media composition of the microaerobic cultures, but all the volumes were halved. The flasks were clamped onto the base plate of a platform shaker (Lab-Line Incubator Shaker) at 37° C. and approximately 180 rpm.

All microaerobic cultures were grown as 100 ml of culture in a 125 ml Erlenmeyer flask. The flask was capped with a rubber stopper pierced with a 22 gauge needle for $CO_2$ exhaust. Similarly, the flasks were clamped onto the base plate of a platform shaker at approximately 180 rpm and 37° C.

All cultures were run as sets which included the control strain growing in the same shaker's incubation conditions, batch of media, and at the same times as each of the other strains being tested. For ethanol and optical density measurements at the first time point, one ml was removed for assays from each flask and placed in a capped 1.5 ml micro-centrifuge tube and cultures were quickly returned to the shaker in order to minimize disruption of growth conditions.

All optical density (OD) measurements throughout the cell physiology studies were done on a ThemoSpectronic Genesys 10uv spectrophotometer at 600 nm. The cultures were diluted 1:10 with the appropriate medium (LB or LB enriched with hydrolysate) in order to maintain the linearity of the OD measurements and read against blanks of the corresponding media. All OD measurements as reported below are the original 1:10 dilution measurements multiplied by 10 to reflect full OD.

Carbon monoxide difference spectra were taken as previously described. Dikshit, K. L., D. A. Webster. "Cloning, characterization and expression of the bacterial globin gene from *Vitreoscilla* in *Escherichia coli*." Gene 70 (1988): 377-386. The majority of carbon monoxide (CO) difference measurements were made under aerobic culture conditions at early stationary phase. All cultures were closely monitored by measurement of OD as cultures approached stationary phase. As OD readings began to level off, 40 ml of the cultures were harvested by centrifugation in a Sorvall Instruments RC5C at 4000 rpm for 10 minutes. Cultures grown under microaerobic conditions were similarly harvested for CO difference measurements immediately after data were collected at the second time point (44-47 hours of growth).

Centrifuge tubes used to spin down cells were weighed before cell culture was added and after cells had been pelleted in order to determine the wet weight of cells. If CO difference was not measured immediately, pellets were stored at −20° C. For CO difference measurement, cells were resuspended at a concentration of 40 mg wet weight of cells per ml in 0.10 M sodium phosphate buffer pH 7.5. Once cells were evenly resuspended, 3 ml of cell suspension was placed into each of two quartz cuvettes. To each cuvette was further added a match head worth of the reducing agent sodium dithionite and cuvettes were mixed by gentle inversion. Both cuvettes were placed into the duel beam spectrophotometer (Varian Cary 300 Scan UV-Visible), the SBW parameter was set to 4.0 and baseline absorbance was measured starting at 600 nm and ending at 400 nm with a scan rate of 200 nm/minute. Then the cuvette positioned toward the front of the machine was removed and bubbled with CO at a rate of approximately one bubble per second for a period of 2 minutes. The CO bubbled cuvette was replaced into the spectrophotometer and sample data was overlaid over the baseline trace with the same scan parameters as the baseline.

Once a CO difference trace had been collected, VHb concentration was determined by measuring absorbance at 419 nm (a positive value) and the absolute value of the absorbance at 436 nm (a negative value) and adding the two values to get AA. Concentration of VHb in nanomoles/ml was determined by $\Delta A/274*1000$. Concentration of VHb in nanomoles/gram cell wet weight was determined by converting nanomoles/ml by multiplying by 1 ml/0.04 g. All VHb concentrations reported herein are in nmoles VHb/g cell wet weight.

All ethanol measurements were made using BioAssay Systems EnzyChrom Ethanol Assay Kit (ECET-100). This enzymatic assay is based on alcohol dehydrogenase catalyzed oxidation of ethanol, in which the NADH formed is coupled to formazan (MTT)/phenazine methosulfate. The intensity of the color produced, measured at 565 nm, is proportionate to the ethanol concentration of the sample. Since this is an enzymatic assay, it requires time to proceed and color is allowed to develop over 5 minutes. Standard curves were prepared for each kit purchased and all ethanol concentrations were determined from the standard curve for the kit used to take measurements. The ECET-100 protocol was followed and reagents were mixed fresh for each sample. OD values at 5 minutes were adjusted by the OD at 5 minutes of the blank (with no ethanol) to determine ethanol concentration, rather than determining the DOD (OD at 5 minutes minus OD at time 0) as described in the protocol. This deviation was due to the relatively large variability in OD at time zero for a sample depending on the time taken to get the cuvette into the spectrophotometer whereas OD changed more slowly around the 5 minute time point. A ThermoSpectronic Genesys 10uv and Brand Ultramicro Cuvettes (Catalog #759200) were used for all ethanol OD measurements. All ethanol measurements reported below are in percentage v/v, unless otherwise specified.

For ethanol measurements, 1 ml was aliquoted from cultures and placed into a 1.5 ml micro-centrifuge tube. The cultures were diluted 100-200 fold, 50 μl in 5 ml dH$_2$O or 50 μl in 10 ml dH$_2$O for ethanol measurement. A blank reaction with all reagents added to a sample of dH$_2$O was prepared for each set of ethanol measurements.

Statistical analysis was done on the data using t-tests to determine the probably that the means of the compared data sets were the same. All probability values provided herein are for two-tailed t-tests. When the number of samples in compared data sets was the same, a paired t-test was used. When the number of samples in compared data sets was different, a t-test with the assumption of homoscedasticity was used because this provided a more conservative probability estimate and there was no reason to believe the variances of the compared data sets were different.

B. VHb Expression Measurements

Figure 7:
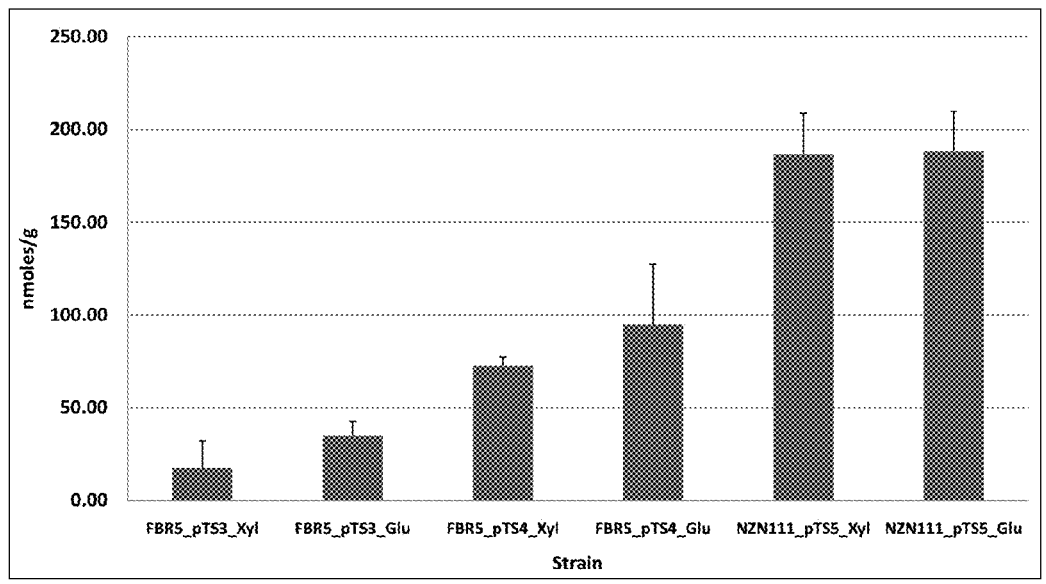
FIG. 7 illustrates a graph which consolidates data from carbon monoxide difference spectra (used for VHb protein expression measurement) which indicated that each strain of ethanol producing *E. coli* expressing VHb ((1) FBR5/pTS3, (2) FBR5/pTS4 and (3) NZN111/pTS5) produced different concentrations of VHb on phosphate buffered LB enriched with 8% (w/v) sugar (aerobic conditions with antibiotics at early stationary phase; measured in nmoles VHb/g wet weight of cells). n equals between 4 and 7; standard deviations indicated.

Once the novel strains of ethanol producing *E. coli* were developed, each strain was grown in phosphate buffered LB media enriched with sugar under aerobic conditions to measure the concentration of VHb production. Mainly aerobic culture conditions were used for the measurement of VHb production by the novel strains because expression of VHb is commonly measured with 50 ml of culture in a 250 ml flask and cells harvested at early stationary phase. The three novel strains were found to produce distinctly different concentrations of VHb on fermentation media (FIG. 7); this allowed examination of the VHb dosage effect on ethanol fermentation. The control strain FBR5 tested negative for VHb expression.

Fermentation Under Microaerobic Conditions with Antibiotics

Figure 9:
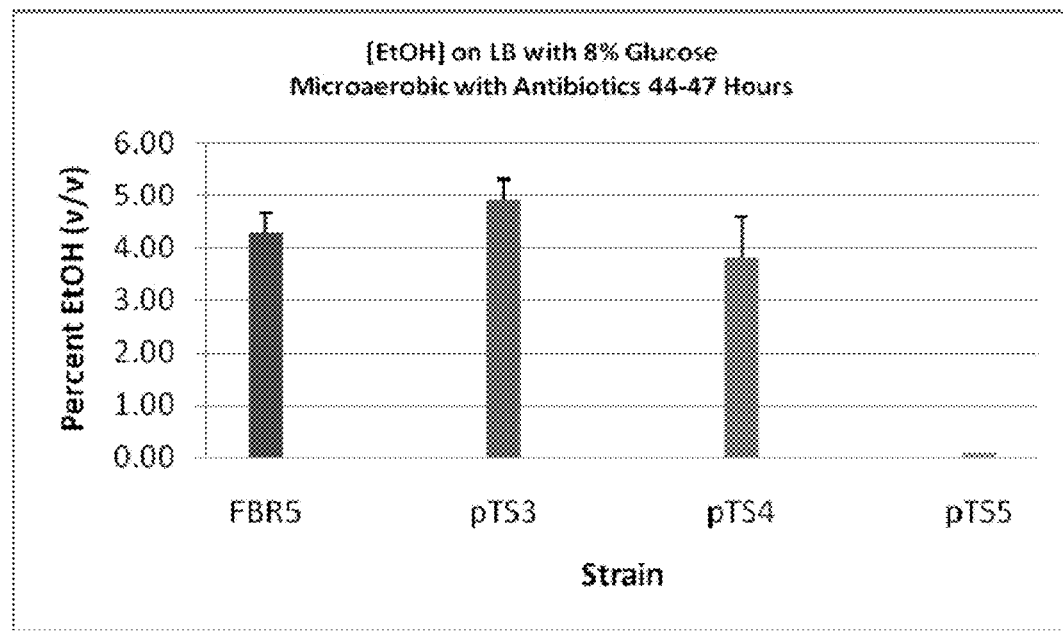
FIG. 9 illustrates a graph of consolidated ethanol assay data ([EtOH] on LB with 8% (w/v) glucose, under microaerobic conditions with antibiotics) which shows that at the 44-47 hour time point the strain FBR5/pTS3 (referred to in the graph as just "pTS3") exceeded the ethanol concentration produced by the FBR5 control, which lacked vgb, by 15% (t-test P-value 0.68%—i.e. approximately 99% confidence). n equals 3; standard deviations indicated.

Fermentation studies were performed with phosphate buffered LB enriched with glucose under microaerobic conditions with antibiotics for the control strain, FBR5, and all three novel strains. FIG. 9 shows that the concentration of ethanol produced by FBR5/pTS3 exceeded the concentration of ethanol produced by FBR5 in phosphate buffered LB with 8% glucose in microaerobic conditions with antibiotics at the 44-47 hour time point by 15%. A t-test provided greater than 99% confidence for this finding of higher ethanol production by FBR5/pTS3 at the 44-47 hour time point.

Figure 12:
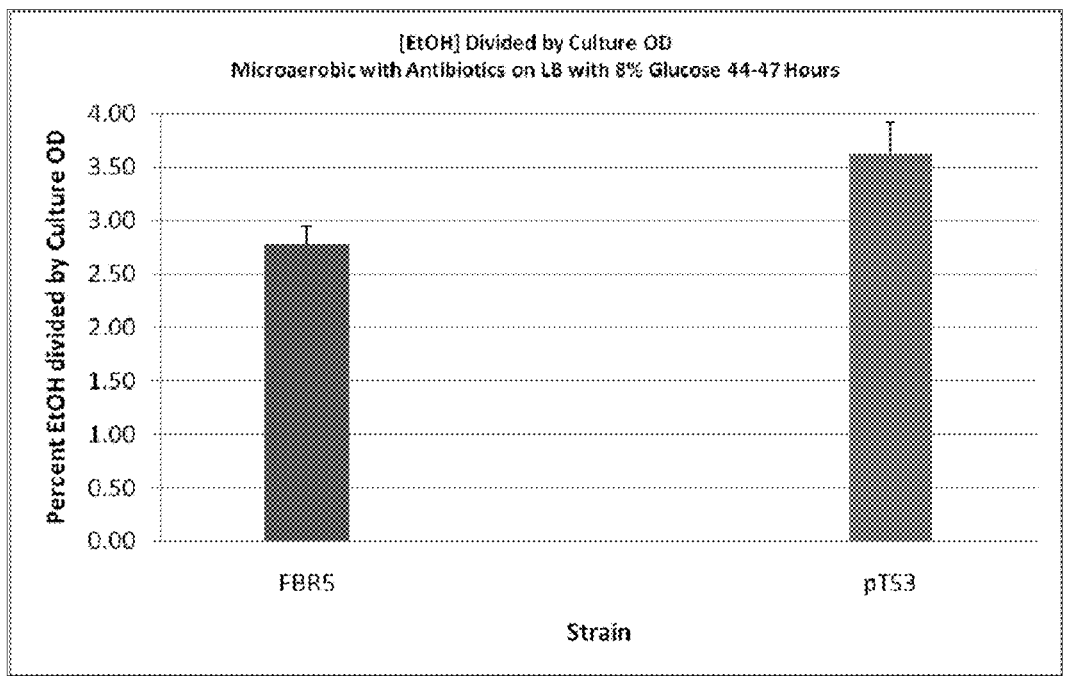
FIG. 12 illustrates a graph of ethanol assay data divided by optical density of cultures (600 nm) indicates that at the 44-47 hour time point FBR5/pTS3 (referred to in the graph as just "pTS3") produced a 31% higher (t-test P-value 8.07%—i.e. approximately 92% confidence) concentration of ethanol per unit measure of cell biomass than the FBR5 control on LB with 8% (w/v) glucose. n equals 3; standard deviations indicated. This graph indicates more efficient production of ethanol on a cell mass basis (i.e. a gram of cells with vgb expression produce more ethanol than a gram of control cells).

The ratio of ethanol concentration to cell biomass was 31% higher for FBR5/pTS3 than FBR5 in phosphate buffered LB with 8% glucose in microaerobic conditions with antibiotics at the 44-47 hour time point (FIG. 12). A t-test provided greater than 90% confidence for this finding. This finding indicates more efficient production of ethanol on a cell mass basis (i.e. a gram of cells with vgb expression produce more ethanol than a gram of control cells).

Since previous measures of VHb expression had been made for aerobic cultures, two sets of measures were made for VHb expression under microaerobic conditions with antibiotics for FBR5/pTS3 and FBR5/pTS4 (FIG. 8). Also, FBR5/pTS3 maintained similar VHb expression levels under microaerobic conditions without antibiotics: on phosphate buffered LB with 8% xylose, 37.38 nmoles VHb/g wet weight of cells, standard deviation 19.12, n equals 3; on phosphate buffered LB with 8% glucose, 54.17 nmoles VHb/g wet weight of cells, standard deviation 13.47, n equals 3.

Fermentation Under Microaerobic Conditions without Antibiotics

Figure 10:
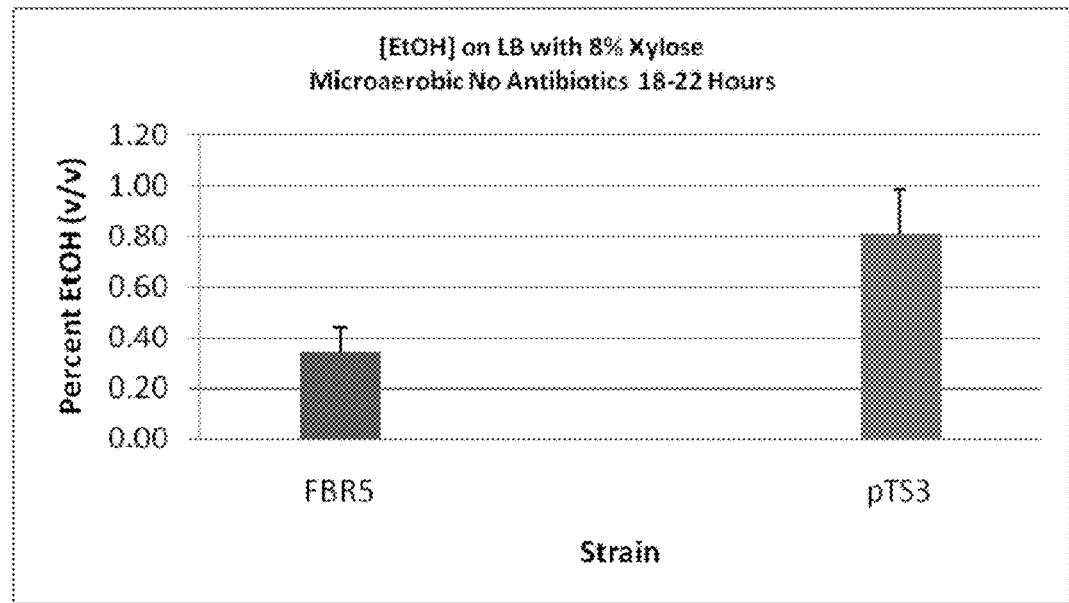
FIG. 10 illustrates a graph of consolidated ethanol assay data ([EtOH] on LB with 8% (w/v) xylose, microaerobic conditions, no antibiotics) which shows that at the 18-22 hour time point the strain FBR5/pTS3 (referred to in the graph as just "pTS3") exceeded the ethanol concentration produced by the FBR5 control, which lacked vgb, by 138% (t-test P-value 1.52%—i.e. approximately 98% confidence). n equals 3; standard deviations indicated.

Additional fermentation studies were performed with phosphate buffered LB enriched with xylose under microaerobic conditions without antibiotics for the control strain, FBR5, and only FBR5/pTS3, because it appeared that the VHb expression level of FBR5/pTS3 was the most beneficial to ethanol production. FIG. 10 shows that the concentration of ethanol produced by FBR5/pTS3 exceeded the concentration of ethanol produced by FBR5 in phosphate buffered LB with 8% xylose in microaerobic conditions without antibiotics at the 18-22 hour time point by 138%. A t-test provided greater than 98% confidence for this finding of higher ethanol production by FBR5/pTS3.

Figure 11:
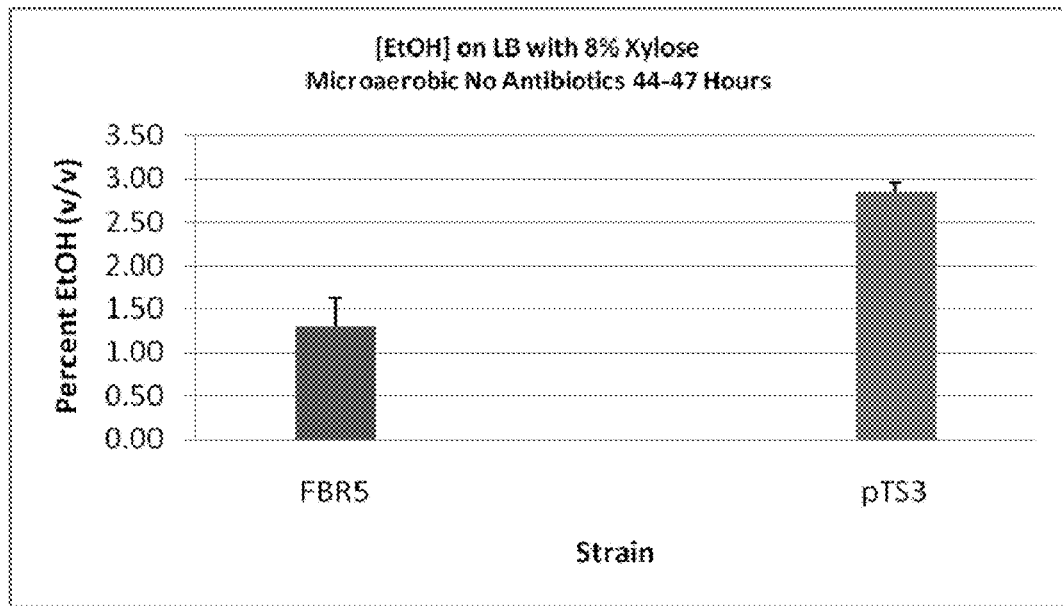
FIG. 11 illustrates a graph of consolidated ethanol assay data ([EtOH] on LB with 8% (w/v) xylose, microaerobic conditions, no antibiotics) which shows that at the 44-47 hour time point the strain FBR5/pTS3 (referred to in the graph as just "pTS3") exceeded the ethanol concentration produced by the FBR5 control, which lacked vgb, by 119% (t-test P-value 1.16%—i.e. approximately 99% confidence). n equals 3; standard deviations indicated.

FIG. 11 shows that the concentration of ethanol produced by FBR5/pTS3 exceeded the concentration of ethanol produced by FBR5 in phosphate buffered LB with 8% xylose in microaerobic conditions without antibiotics at the 44-47 hour time point by 119%. A t-test provided greater than 98% confidence for this finding of higher ethanol production by FBR5/pTS3.

Figure 13:
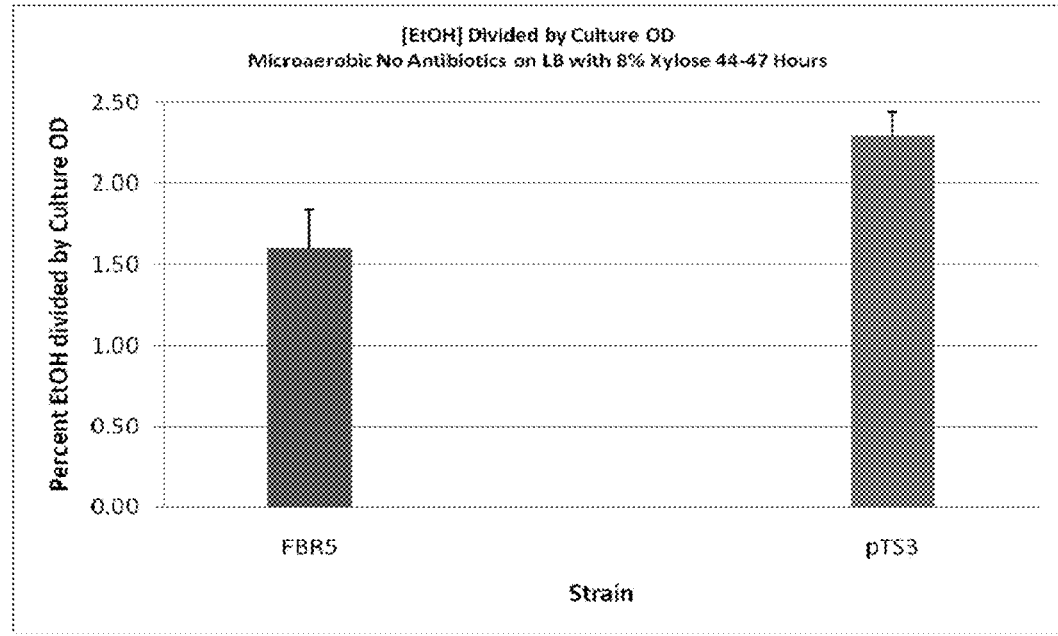
FIG. 13 illustrates a graph of ethanol assay data divided by optical density of cultures (600 nm) indicates that at the 44-47 hour time point FBR5/pTS3 (referred to in the graph as just "pTS3") produced a 44% higher (t-test P-value 2.04%—i.e. approximately 98% confidence) concentration of ethanol per unit measure of cell biomass than the FBR5 control on LB with 8% xylose. n equals 3; standard deviations indicated. This graph also indicates more efficient production of ethanol on a cell mass basis (i.e. a gram of cells with vgb expression produce more ethanol than a gram of control cells).

The ratio of ethanol concentration to cell biomass was 44% higher for FBR5/pTS3 than FBR5 in phosphate buffered LB with 8% xylose in microaerobic conditions without antibiotics at the 44-47 hour time point (FIG. 13). A t-test provided greater than 97% confidence for this finding. This finding indicates more efficient production of ethanol on a cell mass basis (i.e. a gram of cells with vgb expression produce more ethanol than a gram of control cells).

A number of patents, patent application publications, and scientific publications are cited throughout and/or listed at the end of the description. Each of these is incorporated herein by reference in their entirety. Likewise, all publications mentioned in an incorporated publication are incorporated by reference in their entirety.

Examples in cited publications and limitations related therewith are intended to be illustrative and not exclusive. Other limitations of the cited publications will become apparent to those of skill in the art upon a reading of the specification and a study of the drawings.

The words "comprise", "comprises", and "comprising" are to be interpreted inclusively rather than exclusively.

What is claimed is:

1. A method for increasing production of ethanol on a cell-mass basis comprising:
   (a) providing a microorganism of the genus *Saccharomyces* which utilizes a carbon source to produce ethanol wherein said microorganism expresses a xylose isomerase gene;
   (b) genetically modifying said microorganism, wherein said modifying comprises at least one genetic modification which provides for expression of a hemoglobin gene from a bacterium of the genus *Vitreoscilla*, and wherein the expression of the hemoglobin gene from the bacterium of the genus *Vitreoscilla* produces a concentration of intracellular hemoglobin greater than 0 and less than 125 nmoles per gram wet weight of cells; and
   (c) contacting the modified hemoglobin expressing microorganism of step (b) with at least one carbon source comprising xylose under substantially anaerobic conditions,
   wherein production of ethanol is greater on a cell-mass basis after said microorganism is genetically modified to provide for expression of said hemoglobin than before said microorganism is genetically modified to provide for expression of said hemoglobin.

2. The method of claim 1, wherein the expression of the hemoglobin gene from the bacterium of the genus *Vitreoscilla* produces a concentration of intracellular hemoglobin greater than 0 and less than 100 nmoles per gram wet weight of cells.

3. The method of claim 1, wherein the expression of the hemoglobin gene from the bacterium of the genus *Vitreoscilla* produces a concentration of intracellular hemoglobin greater than 0 and less than 75 nmoles per gram wet weight of cells.

4. The method of claim 1, wherein the xylose isomerase gene is an endogenously or heterologously gene.

5. The method of claim 4, wherein the xylose isomerase gene is a wild-type gene, a mutated gene or a purposefully modified gene.

6. The method of claim 4, wherein the xylose isomerase gene is a heterologously gene and wherein said xylose isomerase gene has been inserted into a chromosome of the microorganism.

7. The method of claim 4, wherein the xylose isomerase gene is a heterologously gene and wherein said xylose isomerase gene is in a plasmid or vector.

8. The method of claim 1, wherein the carbon source is derived from cellulosic biomass.

* * * * *